United States Patent
Kamoda et al.

(10) Patent No.: US 10,796,433 B2
(45) Date of Patent: Oct. 6, 2020

(54) INTERPRETATION SUPPORT APPARATUS, OPERATION METHOD THEREOF, AND NON-TRANSITORY COMPUTER READABLE MEDIUM

(71) Applicant: FUJIFILM Corporation, Tokyo (JP)

(72) Inventors: Rena Kamoda, Tokyo (JP); Yuki Okabe, Tokyo (JP); Yusuke Kitagawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 140 days.

(21) Appl. No.: 16/232,813

(22) Filed: Dec. 26, 2018

(65) Prior Publication Data

US 2019/0197684 A1   Jun. 27, 2019

(30) Foreign Application Priority Data

Dec. 27, 2017 (JP) .................. 2017-250793

(51) Int. Cl.
| | |
|---|---|
| G06K 9/00 | (2006.01) |
| G06T 7/00 | (2017.01) |
| G16H 30/40 | (2018.01) |
| G06T 15/00 | (2011.01) |
| A61B 6/03 | (2006.01) |
| A61B 5/055 | (2006.01) |
| G16H 50/20 | (2018.01) |
| G16H 40/63 | (2018.01) |

(52) U.S. Cl.
CPC ............ *G06T 7/0012* (2013.01); *A61B 5/055* (2013.01); *A61B 6/032* (2013.01); *G06T 15/005* (2013.01); *G16H 30/40* (2018.01); *G16H 40/63* (2018.01); *G16H 50/20* (2018.01); *G06T 2200/04* (2013.01); *G06T 2207/30004* (2013.01)

(58) Field of Classification Search
CPC ... A61B 6/32; A61B 5/55; G06T 2207/30004; G06T 2200/04; G06T 7/0012; G06T 15/005; G16H 50/20; G16H 40/63; G16H 30/40
See application file for complete search history.

(56) References Cited

U.S. PATENT DOCUMENTS

| | | | | |
|---|---|---|---|---|
| 2009/0226060 A1* | 9/2009 | Gering | ...................... | G06T 7/11 382/128 |
| 2014/0184608 A1* | 7/2014 | Robb | .................... | A61B 6/5217 345/440 |
| 2016/0110879 A1* | 4/2016 | Garnavi | ................ | G06T 7/0012 382/131 |

FOREIGN PATENT DOCUMENTS

| | | | | |
|---|---|---|---|---|
| JP | 2016-174773 | * | 10/2016 | ............... A61B 6/03 |
| JP | 2016-174773 A | | 10/2016 | |

OTHER PUBLICATIONS

Extended European Search Report dated May 21, 2019, for corresponding European Application No. 18213007.0.

* cited by examiner

*Primary Examiner* — Amara Abdi
(74) *Attorney, Agent, or Firm* — Birch, Stewart, Kolasch & Birch, LLP

(57) ABSTRACT

A screen output control unit of an interpretation support server outputs a viewer screen on which a tissue distribution table is displayed. The tissue distribution table has a first axis, a second axis perpendicular to the first axis, and a first bar mark arranged in a region surrounded by the first axis and the second axis. On the first axis, a plurality of parts of the lung are arranged. On the second axis, a plurality of types of tissues are arranged. The first bar mark expresses the volume of the tissue with a length along the first axis.

19 Claims, 19 Drawing Sheets

FIG. 6

TISSUE DETERMINATION DATA 46

| TISSUE | DETERMINATION CRITERIA |
|---|---|
| NORMAL LUNG | FEATURE AMOUNT Z1 IS EQUAL TO OR GREATER THAN THRESHOLD VALUE T1, ... |
| BRONCHUS | FEATURE AMOUNT Z2 IS LESS THAN THRESHOLD VALUE T2, ... |
| VASCULAR SHADOW | FEATURE AMOUNT Z3 IS EQUAL TO OR GREATER THAN THRESHOLD VALUE T3 AND LESS THAN THRESHOLD VALUE T4, ... |
| GROUND GLASS SHADOW | ... |
| CONSOLIDATION | ... |
| EMPHYSEMA | ... |
| CYST | ... |
| HONEYCOMB LUNG | ... |
| RETICULAR SHADOW | ... |

NORMAL TISSUE: NORMAL LUNG, BRONCHUS, VASCULAR SHADOW

LESION TISSUE:
- FIRST GROUP: GROUND GLASS SHADOW, CONSOLIDATION
- SECOND GROUP: EMPHYSEMA, CYST
- THIRD GROUP: HONEYCOMB LUNG, RETICULAR SHADOW

N SUPPORT APPARATUS, OPERATION METHOD THEREOF, AND NON-TRANSITORY COMPUTER READABLE MEDIUM

CROSS-REFERENCE TO RELATED APPLICATIONS

This application claims priority under 35 U.S.C § 119(a) to Japanese Patent Application No. 2017-250793 filed on 27 Dec. 2017. The above application is hereby expressly incorporated by reference, in its entirety, into the present application.

BACKGROUND OF THE INVENTION

1. Field of the Invention

The present invention relates to an interpretation support apparatus, an operation method thereof, and a non-transitory computer readable medium.

2. Description of the Related Art

In medical facilities, interpretations are actively performed in which doctors observe medical images having three-dimensional information of organs and record findings. A medical image having three-dimensional information of an organ is, for example, a magnetic resonance imaging (MRI; nuclear magnetic resonance imaging method) image or a computed tomography (CT) image. In the related art, in order to support such interpretation, an interpretation support apparatus has been proposed that provides those obtained by analyzing a medical image and processing the analysis result to a doctor for viewing (refer to US2014/0184608A1 and JP2016-174773A).

In US2014/0184608A1 and JP2016-174773A, a CT image of the lung is analyzed to determine to which of a plurality of types of tissues each voxel forming the CT image belongs. US2014/0184608A1 exemplifies emphysema, ground glass shadow, honeycomb lung, normal tissue, and reticular shadow as tissues. JP2016-174773A exemplifies a lesion part (high absorption region) of interstitial pneumonia and a lesion part (low absorption region) of emphysema.

In US2014/0184608A1, a pie chart showing the proportion of tissues for each of a plurality of parts of the lung, such as an upper right lobe and a lower left lobe, is output. In the pie chart, a circle is divided into sectors corresponding to the number of parts, each part is assigned to each sector, each sector is divided into segments corresponding to the number of tissues partitioned by concentric circles, and each tissue is assigned to each segment. The size of the segment is changed according to the number of voxels belonging to each tissue, that is, the volume of each tissue. In US2014/0184608A1, a legend (denoted as color codes in US2014/0184608A1) indicating which tissue is assigned to each segment is output.

In JP2016-174773A, a bar graph showing the proportion of tissues for each of unit blocks (a plurality of parts of the lung) obtained by equally dividing the lung is output. The bar graph is arranged at the position of each unit block corresponding to the illustration of the outline of the lung. For example, a bar graph corresponding to the right lung is arranged on the left side from the center of the illustration, and a bar graph corresponding to the left lung is arranged on the right side from the center. In addition, for example, a bar graph showing the proportion of a lesion part of interstitial pneumonia has an origin at the center, and a bar graph showing the proportion of a lesion part of emphysema has an origin at the left and right ends. The length of the bar graph is changed according to the number of voxels belonging to each tissue, that is, the volume of each tissue. In JP2016-174773A, a legend indicating that each of the bar graph having an origin at the center and the bar graph having an origin at the left and right ends shows the proportion of which tissue is output.

SUMMARY OF THE INVENTION

The doctor performs interpretation focusing on the distribution of tissues, specifically, on what kind of and how many tissues are present in which part. For this reason, the interpretation support apparatus needs to output a distribution that allows the doctor to understand the distribution of tissues at a glance. However, in the interpretation support apparatuses disclosed in US2014/0184608A1 and JP2016-174773A, it has been hard to tell that the doctor can understand the distribution of tissues at a glance just by looking at the pie chart or the bar graph.

This is because, in US2014/0184608A1 and JP2016-174773A, it is not possible to know which tissue is assigned to each segment or which tissue proportion is indicated by each bar graph unless the legend is checked one by one. For this reason, it has been necessary for the doctor to organize the correspondence relationship between each segment and each tissue or the correspondence relationship between each bar graph and each tissue in his or her head.

In US2014/0184608A1, the volume of the tissue is expressed by the size of the segment. In a case where the central angle of each sector is the same (each sector is obtained by equally dividing a circle), this display is relatively easy to understand since the sizes of the segments of the respective sectors can be easily distinguished. However, in US2014/0184608A1, the central angle of each sector is not necessarily the same. For this reason, it is hard to distinguish between the sizes of the segments of the respective sectors, which makes the display rather difficult to understand.

In JP2016-174773A, there is no description regarding to which tissue a region, in which no bar graph is present between the bar graph showing the proportion of a lesion part of interstitial pneumonia and the bar graph showing the proportion of a lesion part of emphysema, corresponds. For this reason, the doctor may be confused.

It is an object of the invention to provide an interpretation support apparatus, an operation method thereof, and a non-transitory computer readable medium capable of allowing a doctor to understand the distribution of tissues at a glance.

In order to achieve the aforementioned object, an interpretation support apparatus of the invention comprises: a reception unit that receives a medical image having three-dimensional information of an organ; an analysis unit that analyzes the medical image to determine to which of a plurality of types of tissues each voxel forming the medical image belongs; and an output control unit that controls an output of a tissue distribution table having a first axis on which a plurality of parts of the organ are arranged, a second axis which is perpendicular to the first axis and on which the tissues are arranged, and a mark that is arranged in a region surrounded by the first and second axes and expresses a magnitude of a volume of each of the tissues according to an analysis result of the analysis unit.

It is preferable that the output control unit outputs a discrete tissue distribution table in which the mark is arranged at an intersection between each of the parts and each of the tissues.

It is preferable that the mark is one of a circle mark expressing the volume with its size, a first bar mark expressing the volume with a length along the first axis, or a second bar mark expressing the volume with a length along the second axis.

It is preferable that the mark is the first bar mark and that the output control unit switches and outputs the discrete tissue distribution table and a combined tissue distribution table in which a combined bar mark, which is obtained by combining the first bar marks along the first axis and expresses a total value of the volume of each of the tissues, is arranged according to an instruction from an operator.

It is preferable that the output control unit outputs an entire tissue proportion display block, which expresses a proportion of the tissue in the entire organ with the first bar mark, at the same time as the tissue distribution table.

It is preferable that the output control unit changes an arrangement order of the tissues on the second axis based on a total value of the volume of each of the tissues. It is preferable that the output control unit changes an arrangement order of the first bar mark in the entire tissue proportion display block based on the total value.

It is preferable that the output control unit outputs a comparative tissue distribution table in which a plurality of marks having different medical images to be analyzed are arranged. In this case, it is preferable that the medical images to be analyzed of the plurality of marks are obtained by imaging the organ of the same patient at different dates and times.

It is preferable that the output control unit outputs the medical image at the same time as the tissue distribution table. In this case, it is preferable that the output control unit arranges the parts on the first axis along a display direction of the organ in the medical image.

It is preferable that the output control unit uses the first axis as a horizontal axis and the second axis as a vertical axis. In this case, it is preferable that the organ is a lung.

It is preferable that the output control unit outputs the mark in an identifiable form for each of the tissues. In this case, it is preferable that the output control unit outputs the tissues on the medical image in the same form as the mark.

It is preferable that the tissues are divided into a plurality of groups according to a pixel value of the voxel and that the output control unit outputs the mark in an identifiable form for each of the groups.

It is preferable that the tissues include a normal tissue and a lesion tissue and that the output control unit outputs the marks arranged in the normal tissue and the marks arranged in the lesion tissue in identifiable forms.

An operation method of an interpretation support apparatus of the invention comprises: a reception step of receiving a medical image having three-dimensional information of an organ; an analysis step of analyzing the medical image to determine to which of a plurality of types of tissues each voxel forming the medical image belongs; and an output control step of controlling an output of a tissue distribution table having a first axis on which a plurality of parts of the organ are arranged, a second axis which is perpendicular to the first axis and on which the tissues are arranged, and a mark that is arranged in a region surrounded by the first and second axes and expresses a magnitude of a volume of each of the tissues according to an analysis result in the analysis step.

A non-transitory computer readable medium for storing a computer-executable program for execution of interpretation support of the invention causes a computer to execute: a reception function for receiving a medical image having three-dimensional information of an organ; an analysis function for analyzing the medical image to determine to which of a plurality of types of tissues each voxel forming the medical image belongs; and an output control function for controlling an output of a tissue distribution table having a first axis on which a plurality of parts of the organ are arranged, a second axis which is perpendicular to the first axis and on which the tissues are arranged, and a mark that is arranged in a region surrounded by the first and second axes and expresses a magnitude of a volume of each of the tissues according to an analysis result of the analysis function.

In the invention, since the tissue distribution table having the first axis on which a plurality of parts of the organ are arranged, the second axis on which a plurality of types of tissues are arranged, and the mark expressing the magnitude of the volume of the tissue is output, it is possible to provide an interpretation support apparatus, an operation method thereof, and a non-transitory computer readable medium capable of allowing a doctor to understand the distribution of tissues at a glance.

BRIEF DESCRIPTION OF THE DRAWINGS

FIG. 6 is a diagram showing tissue determination data.

DESCRIPTION OF THE PREFERRED EMBODIMENTS

First Embodiment

Figure 1:
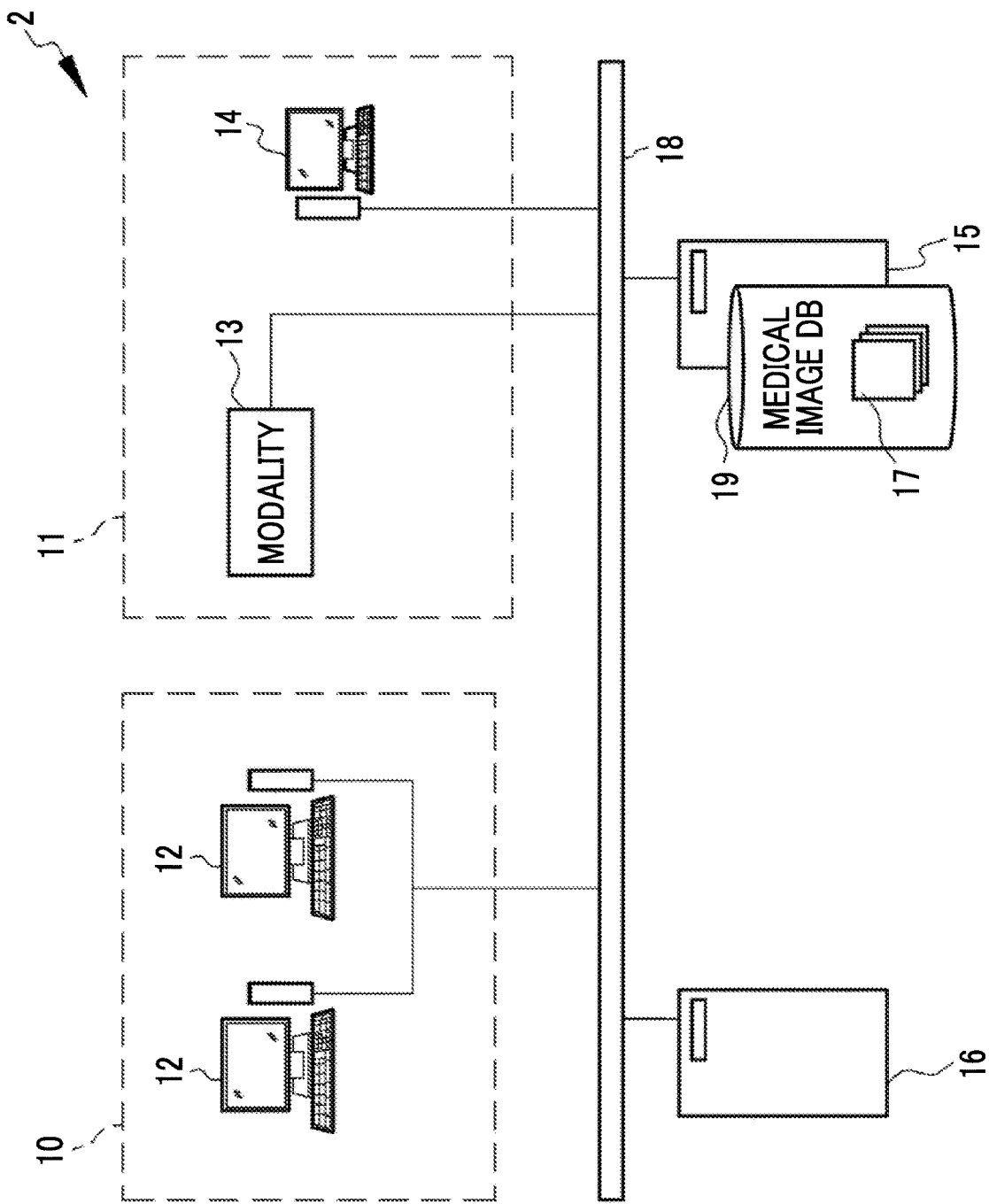
FIG. 1 is a diagram showing a medical information system including an interpretation support server.

In FIG. 1, a medical information system 2 is constructed in a medical facility having a medical department 10 or an examination department 11. The medical information system 2 is configured to include a medical department terminal 12 installed in the medical department 10, a modality 13 and an order management terminal 14 installed in the examination department 11, a medical image database (hereinafter, abbreviated as a database (DB)) server 15, and an interpretation support server 16. The interpretation support server 16 corresponds to an interpretation support apparatus for supporting interpretation in which a doctor DR (refer to FIG. 2) in the medical department 10, who is an operator, observes a medical image 17 captured by modality 13 and records findings. The medical department terminal 12, the modality 13, the order management terminal 14, the medical image DB server 15, and the interpretation support server 16 are connected to each other through a network 18, such as a local area network (LAN) provided in the medical facility.

The medical department terminal 12 is used in a case where the doctor DR inputs or views electronic medical records and a case where the doctor DR issues an examination order for requesting the examination department 11 to make various medical examinations. The medical department terminal 12 is also used also for interpretation.

The modality 13 is an apparatus that captures an image having three-dimensional information of an organ as the medical image 17, for example, a CT apparatus or an MRI apparatus. In the following description, the lung is exemplified as an organ.

The order management terminal 14 receives an examination order issued by the medical department terminal 12, and manages the received examination order. The examination order has various items, for example, an order identification data (ID) for identifying each examination order, an ID of the medical department terminal 12 that issues the examination order or a doctor ID of the doctor DR, a patient ID of a patient (hereinafter, referred to as a target patient) to be imaged according to the examination order, an examination purpose such as follow-up observation, a part to be imaged such as a head and a chest, and orientation such as supine and prone. A technician in the examination department 11 checks the contents of the examination order with the order management terminal 14, and sets the imaging conditions corresponding to the checked examination order in the modality 13 to capture the medical image 17.

In the case of capturing the medical image 17 with the modality 13, information such as the patient ID of the target patient and the technician ID of the technician in charge of imaging is input by the technician. The input information is associated with the medical image 17 as accessory information.

The medical image 17 is created in a data file format based on the digital imaging and communications in medicine (DICOM) standard, for example. In the data file based on the DICOM standard, not only a region for storing the data of the main body of the medical image 17 but also a region for storing the accessory information is provided. The accessory information includes patient information such as a patient ID of a target patient, a patient name, and the gender, age, height, and weight of the patient, examination information such as an order ID, a doctor ID, examination date and time, examination purpose, imaging part and direction, imaging conditions, a technician ID, and the type of medical examination (type of the modality 13, such as CT and MRI), and an image ID for identifying each medical image 17. The image ID is automatically assigned by the modality 13 at the time of capturing the medical image 17. The modality 13 transmits the medical image 17 to the medical image DB server 15.

In the case of a CT apparatus or an MRI apparatus, a plurality of medical images 17 are captured with one examination order. To the plurality of medical images 17, image IDs each including a number or a symbol common to the plurality of medical images 17 and a serial number is assigned. As a result, a plurality of medical images 17 are treated as one set captured according to one examination order.

The medical image DB server 15 is a so-called picture archiving and communication system (PACS) server, and has a medical image DB 19 that stores a plurality of medical images 17 from the modality 13. The medical image DB server 15 transmits the medical image 17 to the medical department terminal 12.

Figure 2:
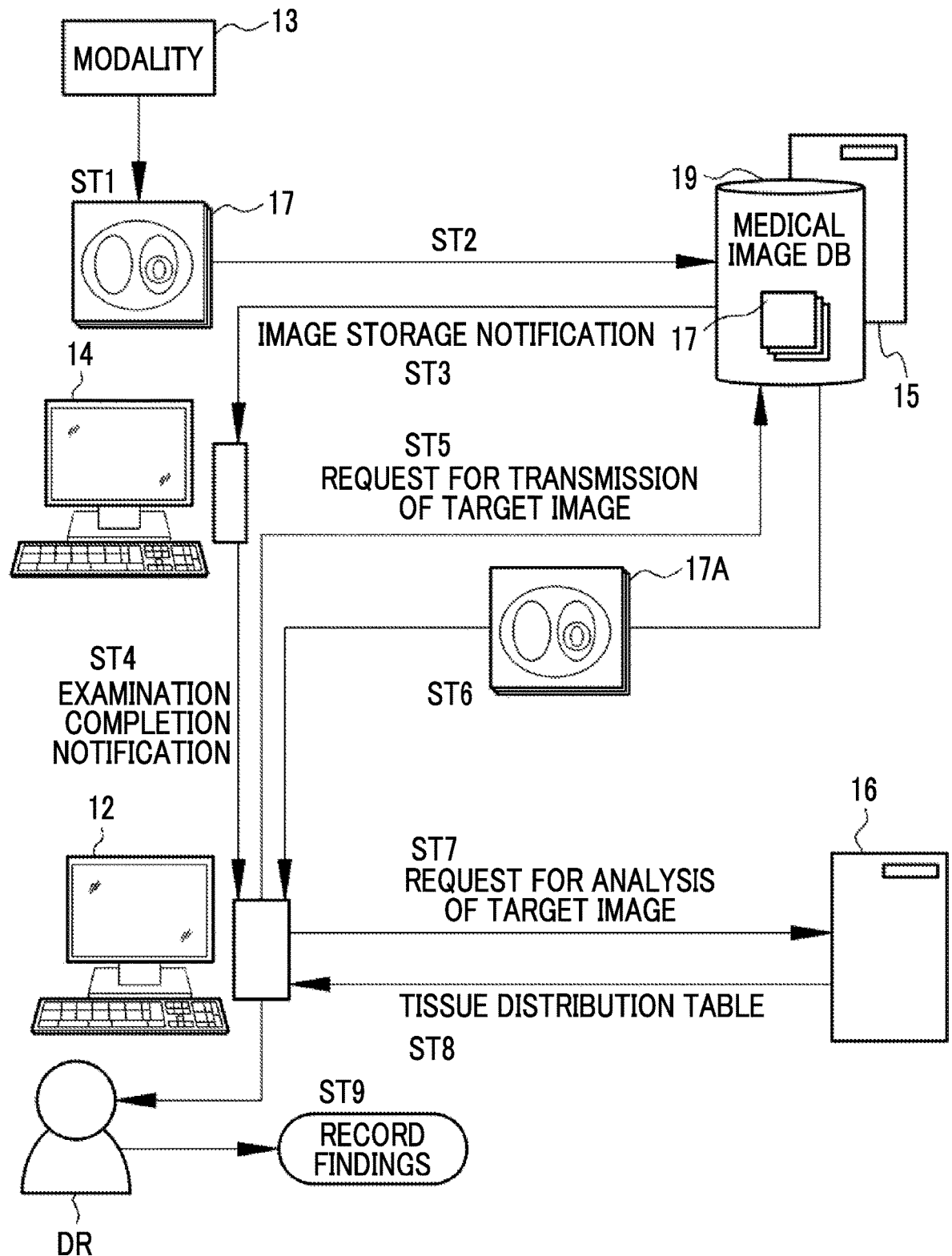
FIG. 2 is an explanatory diagram showing a flow from the start of examination to the end of interpretation.

FIG. 2 shows a flow from the start of examination to the end of interpretation. First, imaging is performed by the modality 13 according to the examination order, and the medical image 17 is output from the modality 13 (step ST1). The medical image 17 is transmitted from the modality 13 to the medical image DB server 15, and is stored in the medical image DB 19 by the medical image DB server 15 (step ST2).

The medical image DB server 15 transmits an image storage notification, which indicates that the medical image 17 has been stored in the medical image DB 19, to the order management terminal 14 (step ST3). In a case where the image storage notification is received, the order management terminal 14 transmits an examination completion notification to the medical department terminal 12 that issued the examination order (step ST4). The image ID or the order ID of the medical image 17 is assigned to the image storage notification and the examination completion notification.

The doctor DR checks the examination completion notification through the medical department terminal 12, and starts interpretation of the medical image 17 including the image ID or the order ID assigned to the examination completion notification. Hereinafter, the medical image 17 to be interpreted will be expressed as a target image 17A.

The doctor DR transmits a request for transmission of the target image 17A to the medical image DB server 15 through the medical department terminal 12 (step ST5). The medical image DB server 15 receives the request for transmission of the target image 17A, and searches for the target image 17A corresponding to the request among the medical images 17 of the medical image DB 19. Then, the searched target image 17A is transmitted to the medical department terminal 12 that transmitted the transmission request (step ST6). The request for transmission of the target image 17A includes various items of accessory information of the medical image 17, for example, an order ID or an image ID. The medical image DB server 15 searches for the medical image 17 matching the order ID or the image ID of the transmission request as the target image 17A.

The medical department terminal 12 displays the target image 17A from the medical image DB server 15. The doctor DR observes the target image 17A through the medical department terminal 12. In a case where the target patient suffers from a certain disease, in addition to the normal tissue, lesion tissue showing the symptoms of the disease appear in the target image 17A. In order to know the distribution of a plurality of types of tissues including the normal tissue and the lesion tissue, the doctor DR transmits a request for analysis of the target image 17A to the interpretation support server 16 through the medical department terminal 12 (step ST7).

The interpretation support server 16 receives the request for analysis of the target image 17A. The interpretation support server 16 analyzes the target image 17A. Then, according to the analysis result, a tissue distribution table 75 (refer to FIG. 10 and the like) showing the distribution of tissues appearing in the target image 17A is output. The interpretation support server 16 transmits the tissue distribution table 75 to the medical department terminal 12 that transmitted the analysis request (step ST8).

The doctor DR views the tissue distribution table 75 through the medical department terminal 12. The doctor DR records findings on the target image 17A based on the tissue distribution table 75, his or her own medical knowledge and experience, and the like (step ST9). Specifically, the findings are a sentence including the name, size (diameter, volume, and the like), and occurrence part of a lesion tissue present in the target image 17A, a disease name analogized from the lesion tissue, and the like. The findings are summarized as an interpretation report together with the target image 17A. The interpretation report is recorded in a report DB (not shown).

The interpretation support server 16 generates a viewer screen 60 (refer to FIGS. 8 and 9) on which the target image 17A and the tissue distribution table 75 are displayed. Then, the generated viewer screen 60 is distributed to the medical department terminal 12. The doctor DR observes the target image 17A and views the tissue distribution table 75 through the viewer screen 60.

The interpretation support server 16 distributes the viewer screen 60 that can be viewed on the web browser. More specifically, the interpretation support server 16 distributes the viewer screen 60 in the form of screen data for web distribution that is created by a markup language, such as Extensible Markup Language (XML). The medical department terminal 12 reproduces and displays the viewer screen 60 on the web browser based on the screen data. Instead of the XML, other data description languages, such as JavaScript (registered trademark) Object Notation (JSON), may be used.

Figure 3:
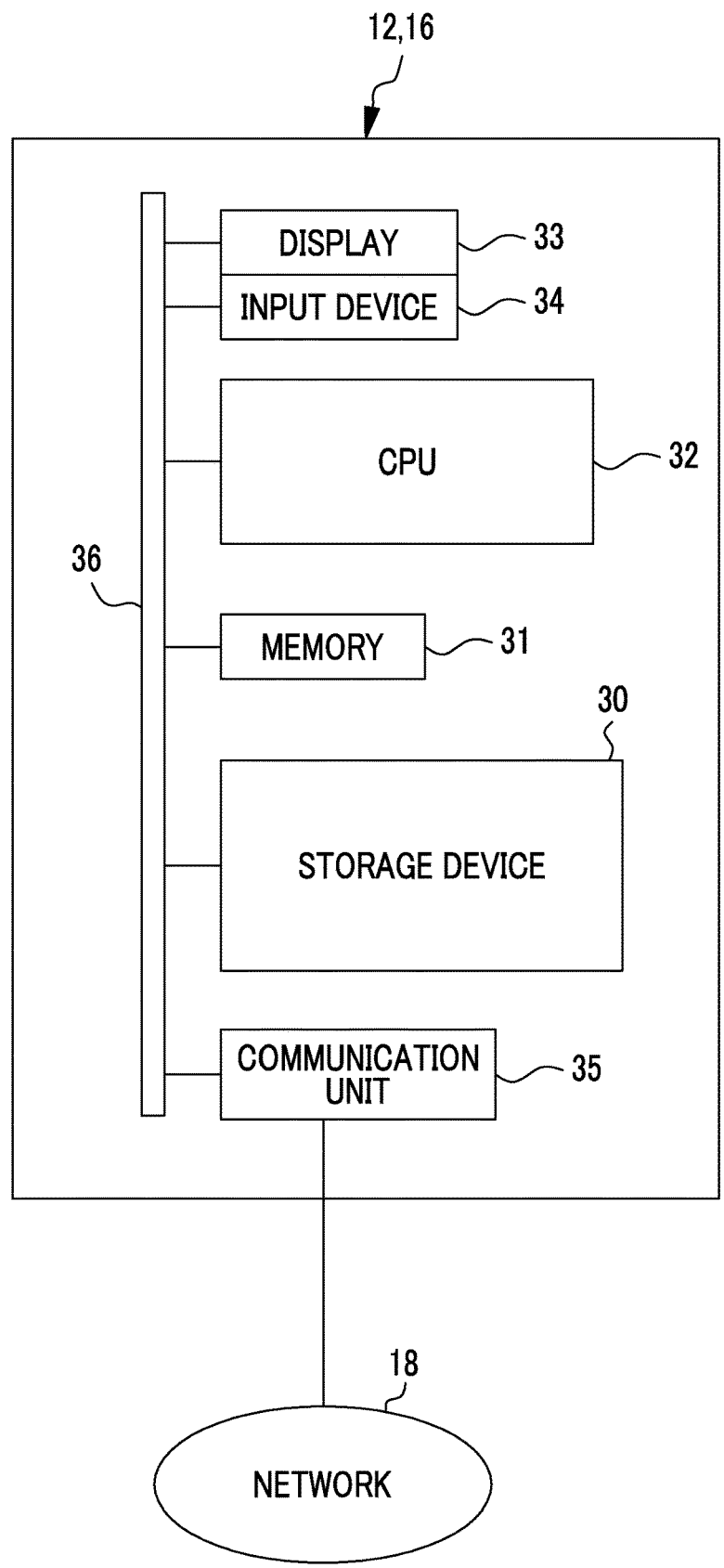
FIG. 3 is a block diagram showing a computer that forms a medical department terminal and an interpretation support server.

In FIG. 3, the basic configurations of computers that form the medical department terminal 12 and the interpretation support server 16 are the same, and each computer comprises a storage device 30, a memory 31, a central processing unit (CPU) 32, a display 33, an input device 34, and a communication unit 35. These are connected to each other through a data bus 36.

The storage device 30 is a hard disk drive, which is built into a computer that forms the medical department terminal 12 or the like or which is connected to the computer through a cable or a network, or a disk array formed by connecting a plurality of hard disk drives. A control program such as an operating system, various application programs, and display data of various screens associated with these programs are stored in the storage device 30.

The memory 31 is a work memory for the CPU 32 to execute processing. The CPU 32 performs overall control of each unit of the computer by loading a program stored in the storage device 30 to the memory 31 and executing the processing according to the program.

The display 33 displays various screens corresponding to the operation of the input device 34. The screen has an operation function based on the graphical user interface (GUI). Each computer that forms the medical department terminal 12 or the like receives an input of an operation instruction from the input device 34 through the screen. The communication unit 35 is a network interface to perform transmission control of various kinds of information through the network 18.

In the following description, for the sake of distinction, a suffix "A" is attached to the reference numeral of each unit of the computer that forms the medical department terminal 12, and a suffix "B" is attached to the reference numeral of each unit of the computer that forms the interpretation support server 16.

Figure 4:
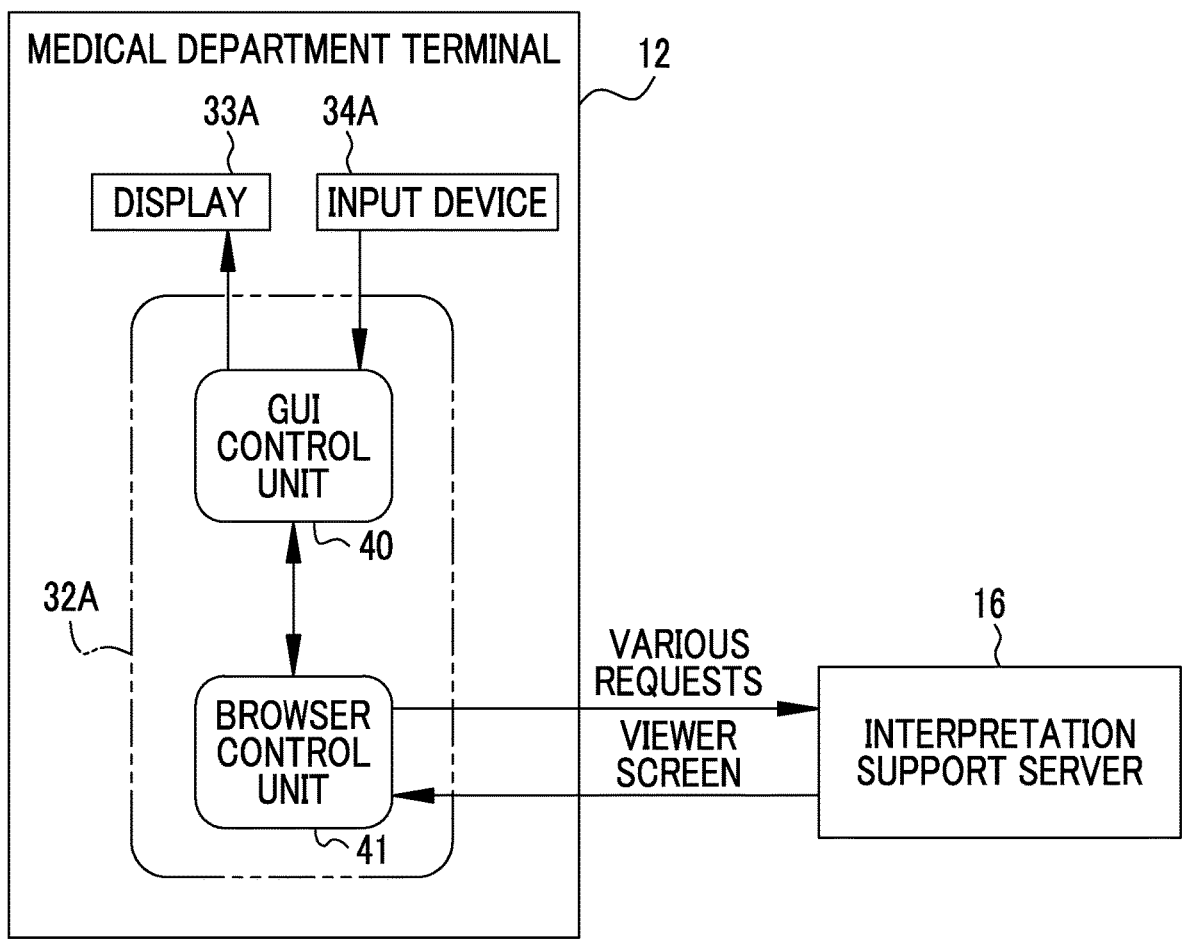
FIG. 4 is a block diagram showing a processing unit constructed in a CPU of a medical department terminal.

In FIG. 4, in a case where a web browser is activated, the CPU 32A of the medical department terminal 12 cooperates with the memory 31 or the like to function as a GUI control unit 40 and a browser control unit 41.

The GUI control unit 40 displays the viewer screen 60 on the display 33A, and receives various operation instructions input from the input device 34A through the viewer screen 60. As the operation instruction, there are an instruction to distribute the viewer screen 60 to the interpretation support server 16, an instruction to analyze the target image 17A, and the like. The GUI control unit 40 outputs the received operation instruction to the browser control unit 41.

The browser control unit 41 controls the operation of the web browser. The browser control unit 41 issues a request corresponding to an operation instruction from the GUI control unit 40, specifically, a request for distribution of the viewer screen 60 corresponding to an instruction to distribute the viewer screen 60, a request for analysis of the target image 17A corresponding to an instruction to analyze the target image 17A, and the like to the interpretation support server 16. The request for distribution of the viewer screen 60 includes the target image 17A. In addition, both the request for distribution of the viewer screen 60 and the request for analysis of the target image 17A include information of the medical department terminal 12 as a request source.

The browser control unit 41 receives screen data of the viewer screen 60 from the interpretation support server 16. The browser control unit 41 reproduces the viewer screen 60 to be displayed on the web browser based on the screen data, and outputs the reproduced viewer screen 60 to the GUI control unit 40. The GUI control unit 40 displays the viewer screen 60 on the display 33A.

Figure 5:
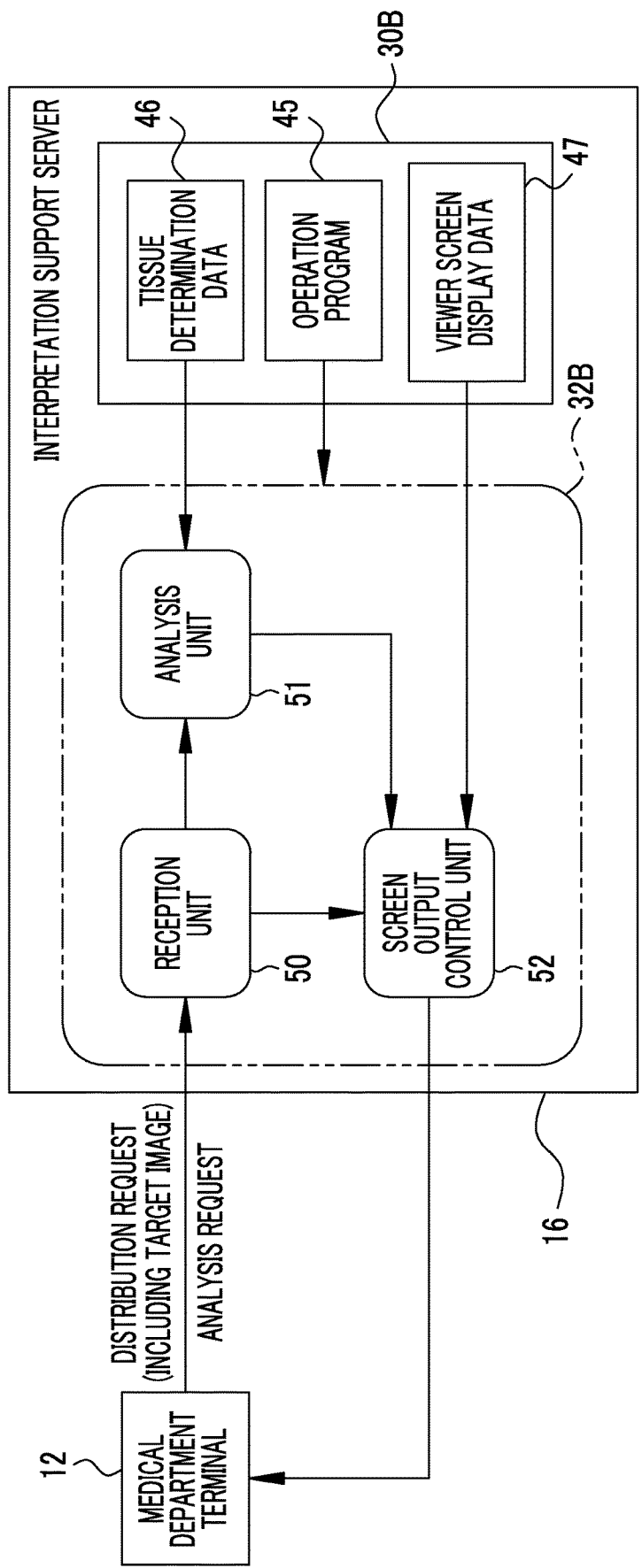
FIG. 5 is a block diagram showing a processing unit constructed in a CPU of an interpretation support server.

In FIG. 5, an operation program 45 is stored in the storage device 30B of the interpretation support server 16. The operation program 45 is an application program for making a computer that forms the interpretation support server 16 function as an interpretation support apparatus. Tissue determination data 46 (refer to FIG. 6) and viewer screen display data 47 (refer to FIG. 7) are also stored in the storage device 30B.

In a case where the operation program 45 is activated, the CPU 32B of the interpretation support server 16 cooperates with the memory 31 or the like to function as a reception unit 50, an analysis unit 51, and a screen output control unit 52.

The reception unit 50 receives the request for distribution of the viewer screen 60 and the request for analysis of the target image 17A from the medical department terminal 12. As described above, the request for distribution of the viewer screen 60 includes the target image 17A. Accordingly, the reception unit 50 has a reception function for receiving the target image 17A (medical image 17). The reception unit 50 outputs the request for distribution of the viewer screen 60 to the screen output control unit 52, and outputs the request for analysis of the target image 17A to the analysis unit 51.

In a case where the request for analysis of the target image 17A is input from the reception unit 50, the analysis unit 51 analyzes the target image 17A with reference to the tissue determination data 46. More specifically, the analysis unit 51 has an analysis function of determining to which of a plurality of types of tissues each voxel forming the target image 17A belongs. The analysis unit 51 outputs the analysis result to the screen output control unit 52.

In a case where the request for distribution of the viewer screen 60 is input from the reception unit 50, the screen output control unit 52 generates the viewer screen 60 (refer to FIG. 8), on which the target image 17A included in the distribution request is displayed, based on the viewer screen display data 47. In a case where the analysis result is input from the analysis unit 51, the screen output control unit 52 generates the viewer screen 60 (refer to FIG. 9), on which the tissue distribution table 75 corresponding to the analysis result is displayed, based on the viewer screen display data 47. Then, the generated viewer screen 60 is distributed to the medical department terminal 12 that is a source of the request for distribution of the viewer screen 60 or the request for analysis of the target image 17A. That is, the screen output control unit 52 has an output control function for controlling the output of the tissue distribution table 75.

In FIG. 6, determination criteria corresponding to respective tissues are registered in the tissue determination data 46. The tissues are a total of nine types of normal lung, bronchus, vascular shadow, ground glass shadow, consolidation, emphysema, cyst, honeycomb lung, and reticular shadow. Among these, three types of normal lung, bronchus, and vascular shadow are normal tissues, and the remaining six types of ground glass shadow, consolidation, emphysema, cyst, honeycomb lung, and reticular shadow are lesion tissues.

The six types of lesion tissues are further divided into first to third groups according to the pixel value of the voxel. Specifically, the ground glass shadow and the consolidation are the first group in which the pixel value of the voxel is relatively high. The emphysema and the cyst are the second group in which the pixel value of the voxel is relatively low. The honeycomb lung and the reticular shadow are the third group in which the pixel value of the voxel is intermediate.

As the determination criteria, for example, conditions based on a feature amount Z, such as "feature amount Z1 is equal to or greater than a threshold value Ti" and "feature amount Z3 is equal to or greater than a threshold value T3 and less than a threshold value T4", are registered. There are a plurality of kinds of feature amounts Z as indicated by Z1, Z2, and the like. The feature amount Z is, for example, a pixel value of a small region of a unit cube of one to several voxels, or an average value, a maximum value, a minimum value, a mode value, or a standard deviation thereof.

First, the analysis unit 51 recognizes a portion of the lung from the target image 17A. Then, the feature amount Z of each small region of the recognized portion of the lung is calculated. Then, based on the calculated feature amount Z and the tissue determination data 46, the tissue to which each small region belongs is determined. The analysis unit 51 outputs the coordinate information of the recognized portion of the lung and information, in which the coordinate information of each small region and the tissue to which each small region belongs are associated with each other, to the screen output control unit 52 as an analysis result.

Here, it is determined that a plurality of tissues are mixed in some of the small regions. In this case, a plurality of tissues are written together in the information in which the coordinate information of each small region and the tissue to which each small region belongs are associated with each other.

A machine learning algorithm, such as adaptive boosting (AdaBoost) or deep learning, may be used for determination of tissue. For example, a plurality of sets of voxels whose tissues are determined and the feature amounts Z or a plurality of medical images 17 themselves are input as sample data, and the relationship between the tissues and the feature amounts Z are learned in the machine learning algorithm. Then, the tissue corresponding to the calculated feature amount Z is made to reply to the machine learning algorithm.

Figure 7:
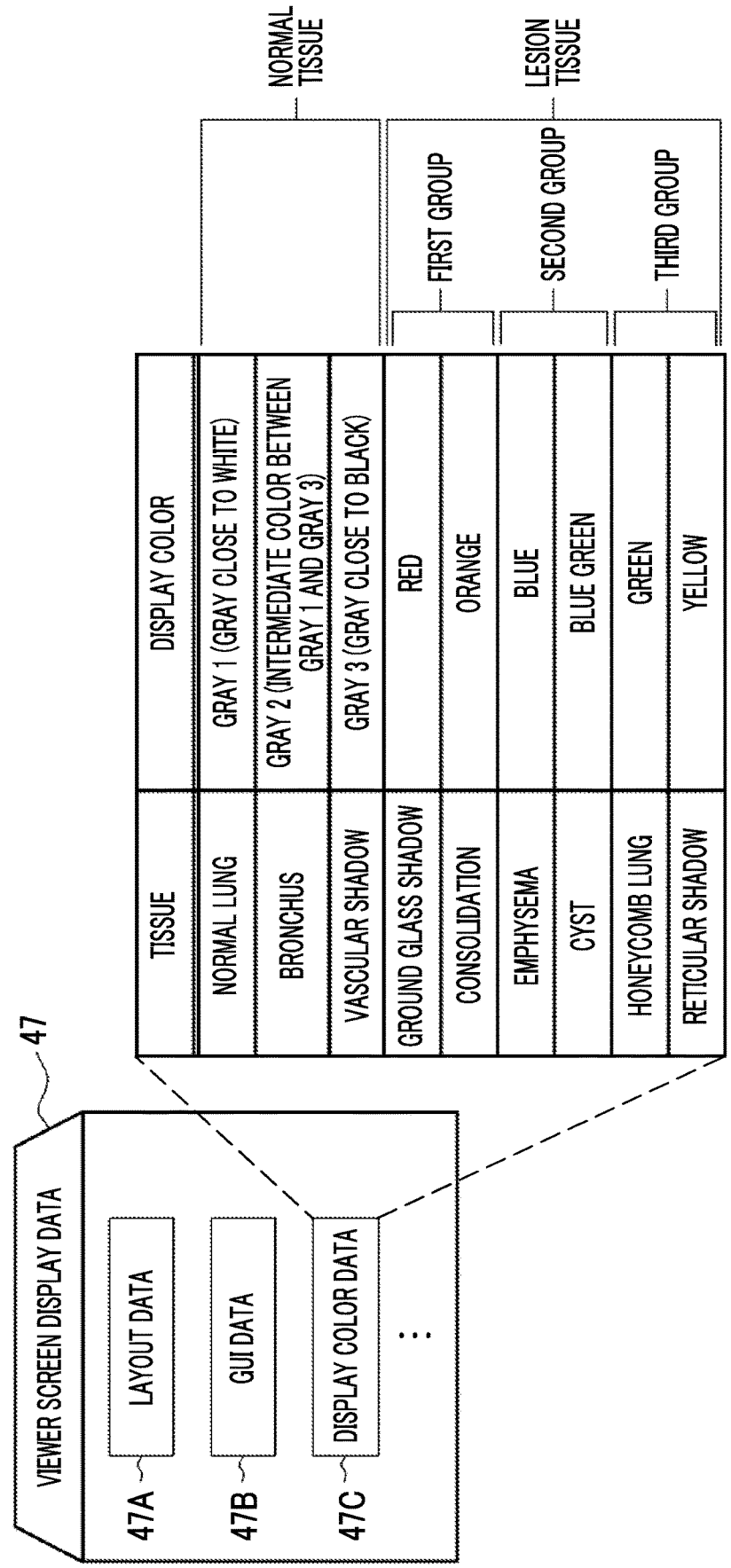
FIG. 7 is a diagram showing viewer screen display data.

In FIG. 7, the viewer screen display data 47 includes layout data 47A, GUI data 47B, display color data 47C, and the like. The layout data 47A is literally data for defining the layout of the viewer screen 60. The target image 17A and the tissue distribution table 75 are laid out on the viewer screen 60 according to the layout data 47A. The GUI data 47B is GUI data, such as icons 68 to 70 (refer to FIG. 8) arranged on the viewer screen 60.

The display color data 47C is data in which the display color of each tissue in the tissue distribution table 75 and the target image 17A is registered. Different colors are assigned as display colors of respective tissues so that these tissues can be distinguished in the tissue distribution table 75 and the target image 17A. For example, in order to make it possible to distinguish between a normal tissue and a lesion tissue in the tissue distribution table 75 and the target image 17A, an achromatic color is assigned as the display color of the normal tissue and a chromatic color is assigned as the display color of the lesion tissue. More specifically, achromatic colors, such as gray 1 (gray close to white, normal lung), gray 2 (intermediate color between gray 1 and gray 3, bronchus), and gray 3 (gray close to black, vascular shadow), are assigned to the normal tissue. On the other hand, chromatic colors, such as red (ground glass shadow), blue (emphysema), and yellow (reticular shadow), are assigned to the lesion tissue.

In addition, in order to make it possible to distinguish among the first to third groups in the tissue distribution table 75 and the target image 17A, a warm color is assigned as the display color of the first group, a cold color is assigned as the display color of the second group, and a neutral color is assigned as the display color of the third group. More specifically, warm colors, such as red (ground glass shadow) and orange (consolidation), are assigned to the first group. Cold colors, such as blue (emphysema) and blue green (cyst), are assigned to the second group. Neutral colors, such as green (honeycomb lung) and yellow (reticular shadow), are assigned to the third group.

Figure 8:
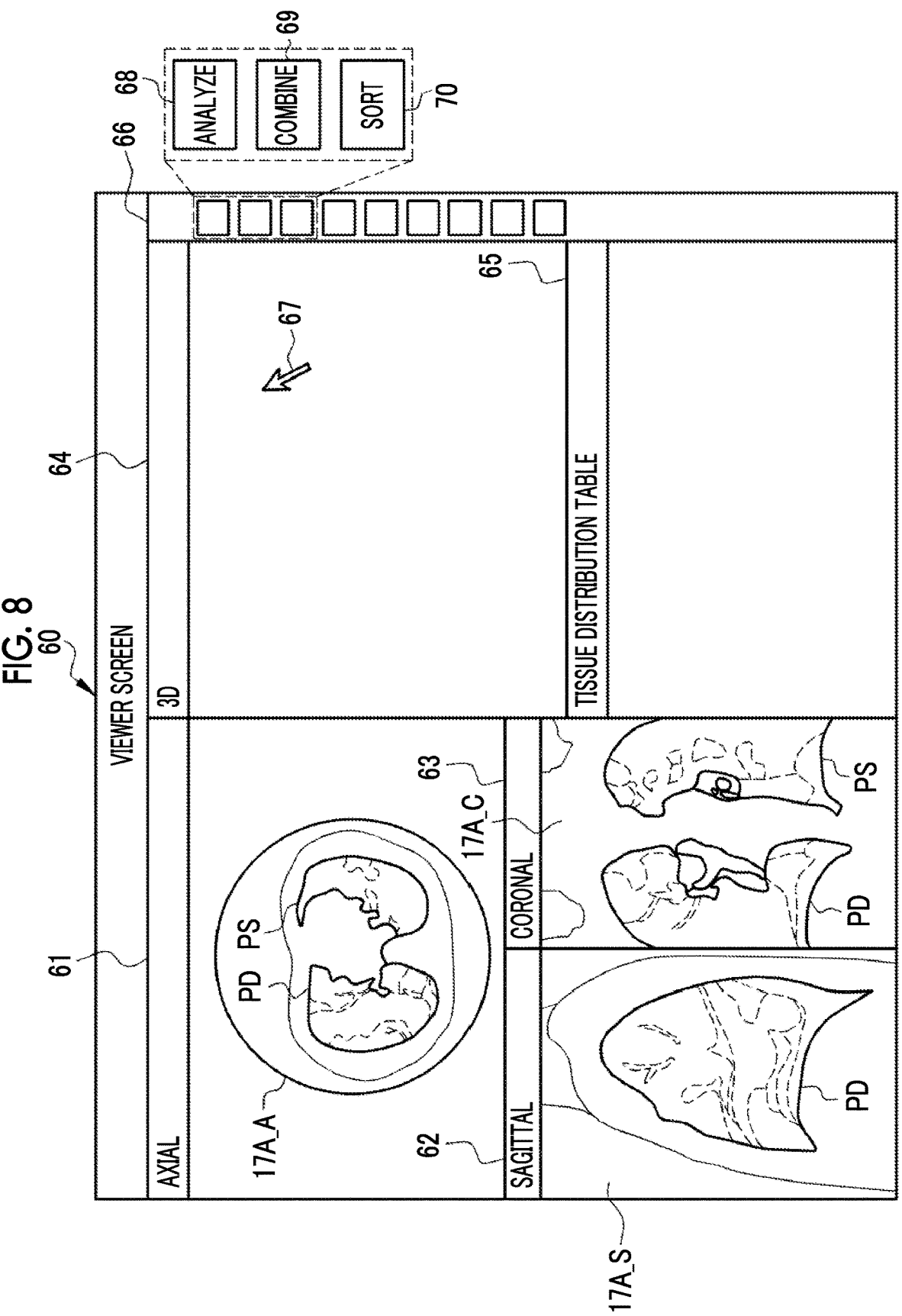
FIG. 8 is a diagram showing a viewer screen before giving an instruction to analyze a target image.

In response to the request for distribution of the viewer screen 60, first, the screen output control unit 52 outputs the viewer screen 60 shown in FIG. 8.

In FIG. 8, the viewer screen 60 has an axial image display region 61, a sagittal image display region 62, a coronal image display region 63, a first analysis result display region 64, a second analysis result display region 65, and a tool bar 66.

The target image 17A of an axial cross section that is a cross section obtained by horizontally cutting the body, that is, an axial image 17A_A, is arranged in the axial image display region 61. The target image 17A of a sagittal cross section that is a cross section obtained by vertically cutting the body, that is, a sagittal image 17A_S, is arranged in the sagittal image display region 62. The target image 17A of a coronal cross section that is a cross section obtained by traversing the body, that is, a coronal image 17A_C, is arranged in the coronal image display region 63.

The axial image 17A_A, the sagittal image 17A_S, and the coronal image 17A_C are images obtained by imaging the chest as an imaging part in a state in which the target patient is supine. A left lung PS (pulmo sinister) is shown on the right side of the axial image 17A_A and the coronal image 17A_C, and a right lung PD (pulmo dexter) is shown on the left side of the axial image 17A_A and the coronal image 17A_C. The right lung PD is shown in the sagittal image 17A_S. In the axial image 17A_A, the sagittal image 17A_S, and the coronal image 17A_C, it is possible to change the position of the cross section or to change the display direction.

Nothing is displayed in the first analysis result display region 64 and the second analysis result display region 65 in the display initial stage of the viewer screen 60 shown in FIG. 8.

Various icons, such as an analysis instruction icon 68, a combination instruction icon 69, and a sort instruction icon 70 based on the GUI data 47B, are arranged on the tool bar 66. These can be selected by a cursor 67.

The analysis instruction icon 68 is a GUI for giving an instruction to analyze the target image 17A. In a case where the analysis instruction icon 68 is selected by the cursor 67, a request for analysis of the target image 17A is issued from the browser control unit 41 of the medical department terminal 12 to the reception unit 50 of the interpretation support server 16. The screen output control unit 52 outputs the viewer screen 60 shown in FIG. 9 in response to the request for analysis of the target image 17A.

Figure 9:
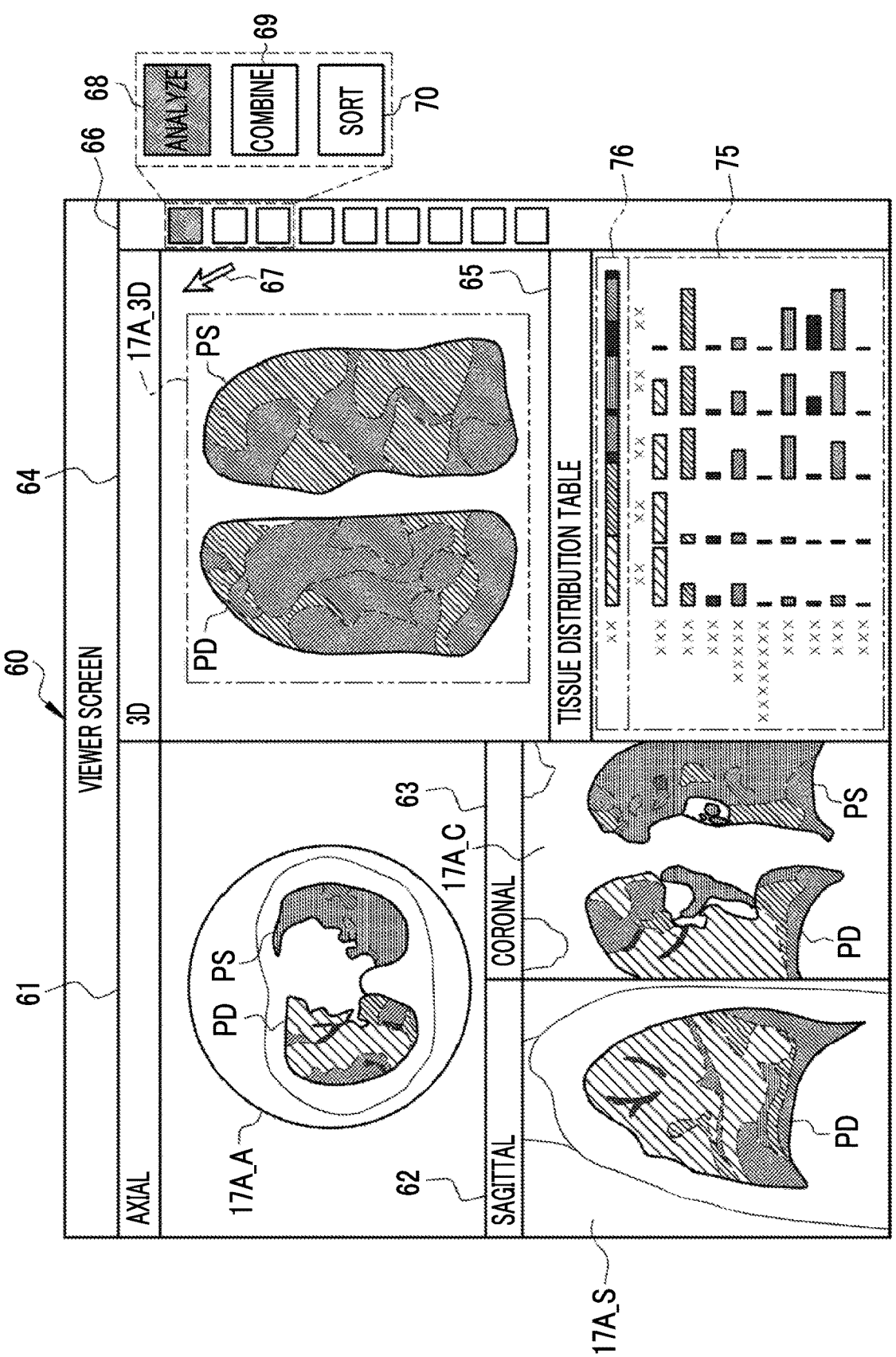
FIG. 9 is a diagram showing a viewer screen after giving an instruction to analyze a target image.

In FIG. 9, a three-dimensional image 17A_3D obtained by extracting a portion of the lung in the target image 17A and displaying the portion of the lung in a three-dimensional manner is arranged in the first analysis result display region 64. The screen output control unit 52 generates the three-dimensional image 17A_3D based on the coordinate information of the portion of the lung recognized by the analysis unit 51. Similarly to the axial image 17A_A and the coronal image 17A_C, the left lung PS is shown on the right side of the three-dimensional image 17A_3D, and the right lung PD is shown on the left side of the three-dimensional image 17A_3D.

As shown by hatching, the screen output control unit 52 colors the portion of the lung in each of the images 17A_A, 17A_S, and 17A_C arranged in the image display regions 61 to 63 and the three-dimensional image 17A_3D arranged in the first analysis result display region 64, for each tissue, based on the display color data 47C shown in FIG. 7. For a small region determined to include a plurality of tissues by the analysis unit 51, coloring is performed according to one representative tissue among the plurality of tissues.

In FIG. 9, coloring for each tissue is drawn roughly. However, the coloring is performed in units of small regions for which the feature amount Z is calculated. In practice, therefore, the coloring is performed more finely.

The tissue distribution table 75 and an entire tissue proportion display block 76 are arranged in the second analysis result display region 65. The screen output control unit 52 generates the tissue distribution table 75 and the entire tissue proportion display block 76 based on the information from the analysis unit 51, in which the coordinate information of each small region and the tissue to which each small region belongs are associated with each other.

As shown by hatching, the analysis instruction icon 68 is displayed so as to be distinguishable from the non-selection case of FIG. 8, so that it can be seen that the analysis instruction icon 68 has been selected by the cursor 67. In a case where the analysis instruction icon 68 is selected again by the cursor 67 in the selection state of FIG. 9, the selection is canceled. Similarly for the other icons 69 and 70, selection and non-selection are displayed so as to be distinguishable, and the selection of the other icons 69 and 70 is canceled by selecting the other icons 69 and 70 again. In a case where the selection of the analysis instruction icon 68 is canceled in FIG. 9, the screen output control unit 52 returns the viewer screen 60 to the state of FIG. 8.

Figure 10:
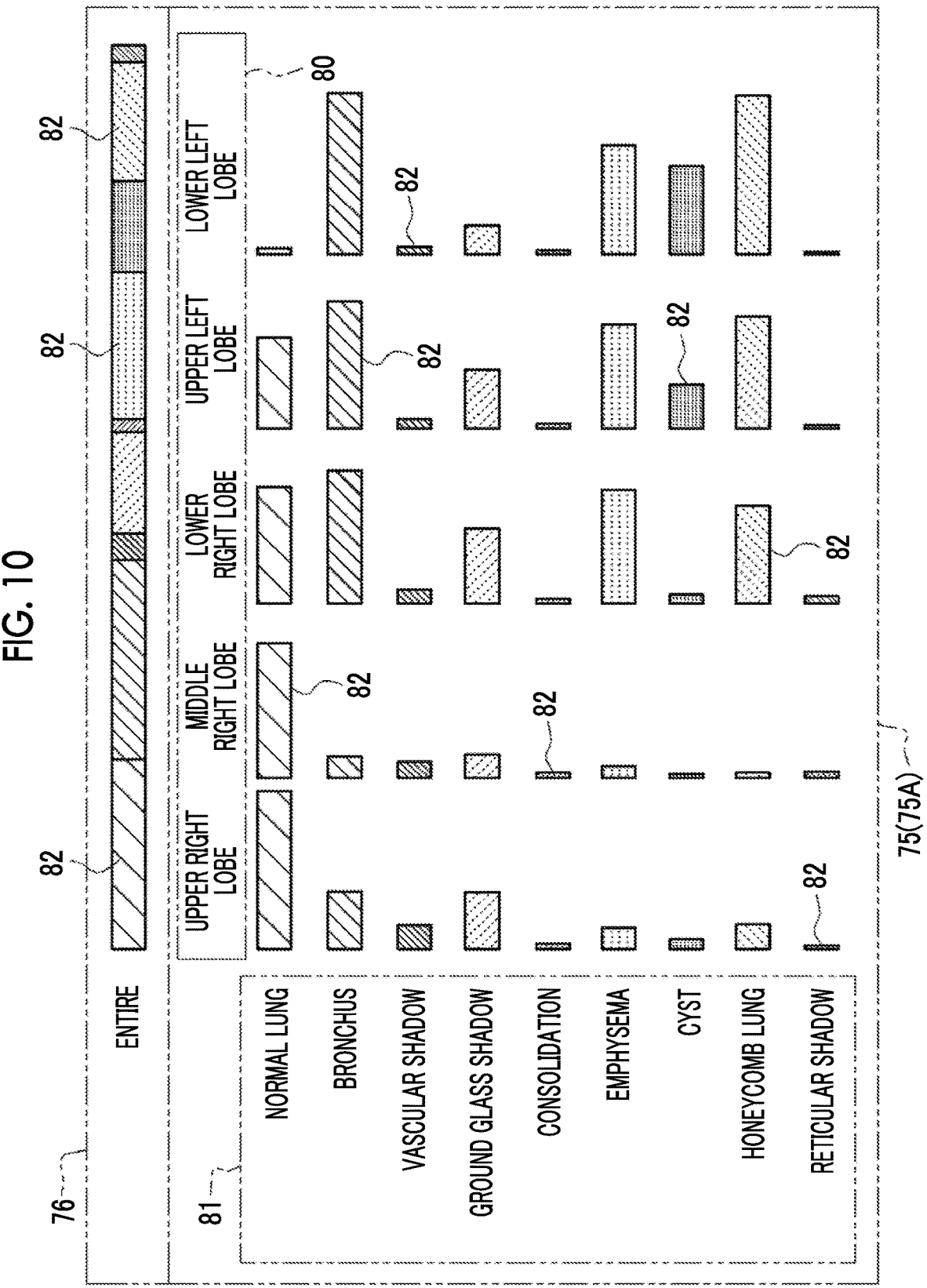
FIG. 10 is a diagram showing a tissue distribution table and an entire tissue proportion display block.

In FIG. 10, the tissue distribution table 75 has a first axis 80 as a horizontal axis, a second axis 81 as a vertical axis perpendicular to the first axis 80, and a first bar mark 82 arranged in a region surrounded by the first axis 80 and the second axis 81.

On the first axis 80, a total of five lung parts of an upper right lobe, a middle right lobe, a lower right lobe, an upper left lobe, and a lower left lobe are arranged in this order. The upper right lobe, the middle right lobe, and the lower right lobe are literally an upper part, a middle part and a lower part of the right lung PD, and the upper left lobe and the lower left lobe are literally an upper part and a lower part of the left lung PS.

The screen output control unit 52 arranges the parts on the first axis along the display direction of the lung in the target image 17A. In this example, the left lung PS is shown on the right side of the axial image 17A_A and the coronal image 17A_C, and the right lung PD is shown on the left side of the axial image 17A_A and the coronal image 17A_C. For this reason, the screen output control unit 52 arranges the upper left lobe and the lower left lobe on the right side of the first axis 80, and arranges the upper right lobe, the middle right lobe, the lower right lobe on the left side of the first axis 80.

On the second axis 81, a total of nine types of tissues such as a normal lung and a ground glass shadow shown in FIGS. 6 and 7 are arranged. As the arrangement order, normal tissues such as a normal lung are located at upper positions, and lesion tissues such as a ground glass shadow are located at lower positions. As the arrangement order of groups, the first group including the ground glass shadow and the like is located at the upper position, the second group including emphysema and the like is located at the middle position, and the third group including the honeycomb lung is located at the lower position.

The screen output control unit 52 counts the number of voxels belonging to each tissue in each part based on the information from the analysis unit 51, in which the coordinate information of each small region and the tissue to which each small region belongs are associated with each other. The number of voxels belonging to each tissue in each part indicates the volume of each tissue in each part. The first bar mark 82 is a mark expressing the magnitude of the volume of the tissue according to the analysis result of the analysis unit 51. Specifically, the first bar mark 82 expresses the number of voxels belonging to each tissue in each part with a length along the first axis 80 as the volume of each tissue in each part. That is, the number of voxels belonging to each tissue increases (the volume of the tissue increases) as the length along the first axis 80 increases, and the number of voxels belonging to each tissue decreases (the volume of the tissue decreases) as the length along the first axis 80 decreases.

For a small region determined to include a plurality of tissues by the analysis unit 51, the screen output control unit 52 counts the number of voxels of the small region in each of the determined plurality of tissues.

As shown by hatching, the screen output control unit 52 colors the first bar mark 82 based on the display color data 47C shown in FIG. 7 for each tissue. In the display color data 47C, different colors are assigned to respective tissues as display colors. Therefore, it can be said that the screen output control unit 52 outputs the first bar mark 82 in an identifiable form for each tissue. In the display color data 47C, an achromatic color is assigned as the display color of the normal tissue and a chromatic color is assigned as the display color of the lesion tissue. Therefore, it can be said that the screen output control unit 52 outputs the first bar mark 82 arranged in the normal tissue and the first bar mark 82 arranged in the lesion tissue in identifiable forms. In addition, in the display color data 47C, a warm color is assigned as the display color of the first group, a cold color is assigned as the display color of the second group, and a neutral color is assigned as the display color of the third group. Therefore, it can be said that the screen output control unit 52 outputs the first bar mark 82 in an identifiable form for each group.

As shown in FIG. 9, the screen output control unit 52 also colors the portion of the lung in each of the images 17A_A, 17A_S, and 17A_C for each tissue. Therefore, it can be said that the screen output control unit 52 outputs the tissue on the target image 17A (medical image 17) in the same form as the first bar mark 82.

In the tissue distribution table 75 shown in FIG. 10, the first bar mark 82 is arranged at the intersection between each part on the first axis 80 and each tissue on the second axis 81. Therefore, the tissue distribution table 75 shown in FIG. 10 corresponds to a discrete tissue distribution table. Hereinafter, reference numeral 75A is given to the discrete tissue distribution table.

The entire tissue proportion display block 76 expresses the proportion of each tissue in the entire lung with the first bar mark 82. The first bar mark 82 of each tissue in the entire tissue proportion display block 76 expresses the magnitude of the proportion of each tissue with a length along the first axis 80. For example, in a case where the number of voxels of the entire lung is 1000 and the number of voxels of the normal lung is 500, the first bar mark 82 of the normal lung has a length occupying 50% of the entire tissue proportion display block 76.

The first bar marks 82 of the respective tissues in the entire tissue proportion display block 76 are arranged in the same arrangement order as the second axis 81 from the left to the right. Specifically, the first bar mark 82 of the normal lung is located at the left end, the first bar marks 82 of the bronchus, the vascular shadow, the ground glass shadow, . . . are located subsequent thereto, and the first bar mark 82 of the reticular shadow is finally arranged at the right end.

Figure 11:
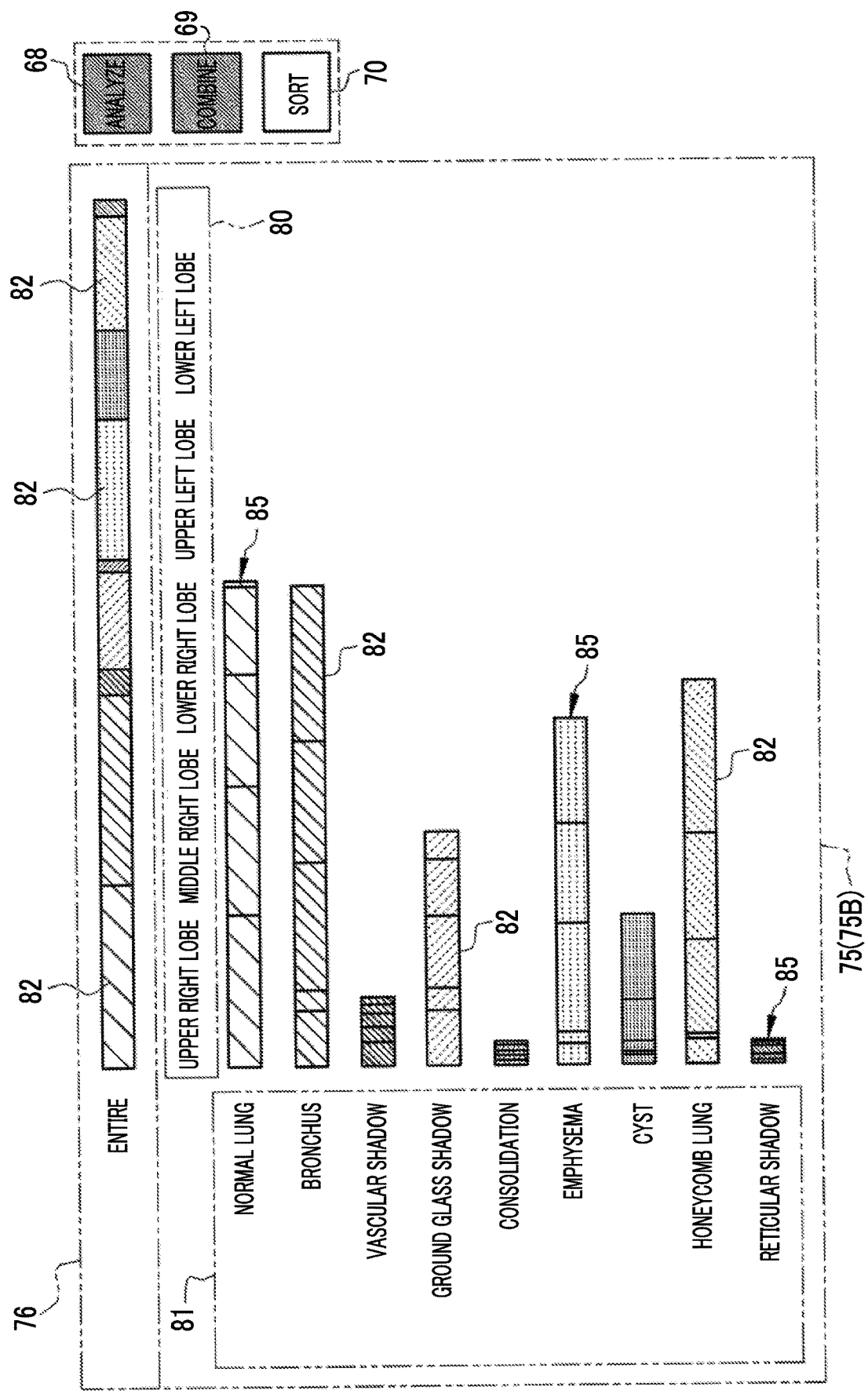
FIG. 11 is a diagram showing a tissue distribution table and an entire tissue proportion display block in a case where a combination instruction icon is selected.

In a case where the combination instruction icon 69 is selected by the cursor 67, the screen output control unit 52 changes the display of the tissue distribution table 75 as shown in FIG. 11. Specifically, the screen output control unit 52 combines the first bar marks 82 arranged at the intersections between the parts on the first axis 80 and the tissues on the second axis 81 by leftward filling along the first axis 80, thereby forming one combined bar mark 85. The display of each part on the first axis 80 is left as it is. The combined bar mark 85 expresses the total value of the volume of each tissue. The tissue distribution table 75 shown in FIG. 11 corresponds to a combined tissue distribution table. Hereinafter, reference numeral 75B is given to the combined tissue distribution table.

In a case where the selection of the combination instruction icon 69 is canceled in FIG. 11, the screen output control unit 52 returns the state to the state of the discrete tissue distribution table 75A shown in FIG. 10. That is, the screen output control unit 52 switches and outputs the discrete tissue distribution table 75A shown in FIG. 10 and the combined tissue distribution table 75B shown in FIG. 11 according to the instruction from the doctor DR.

Figure 12:
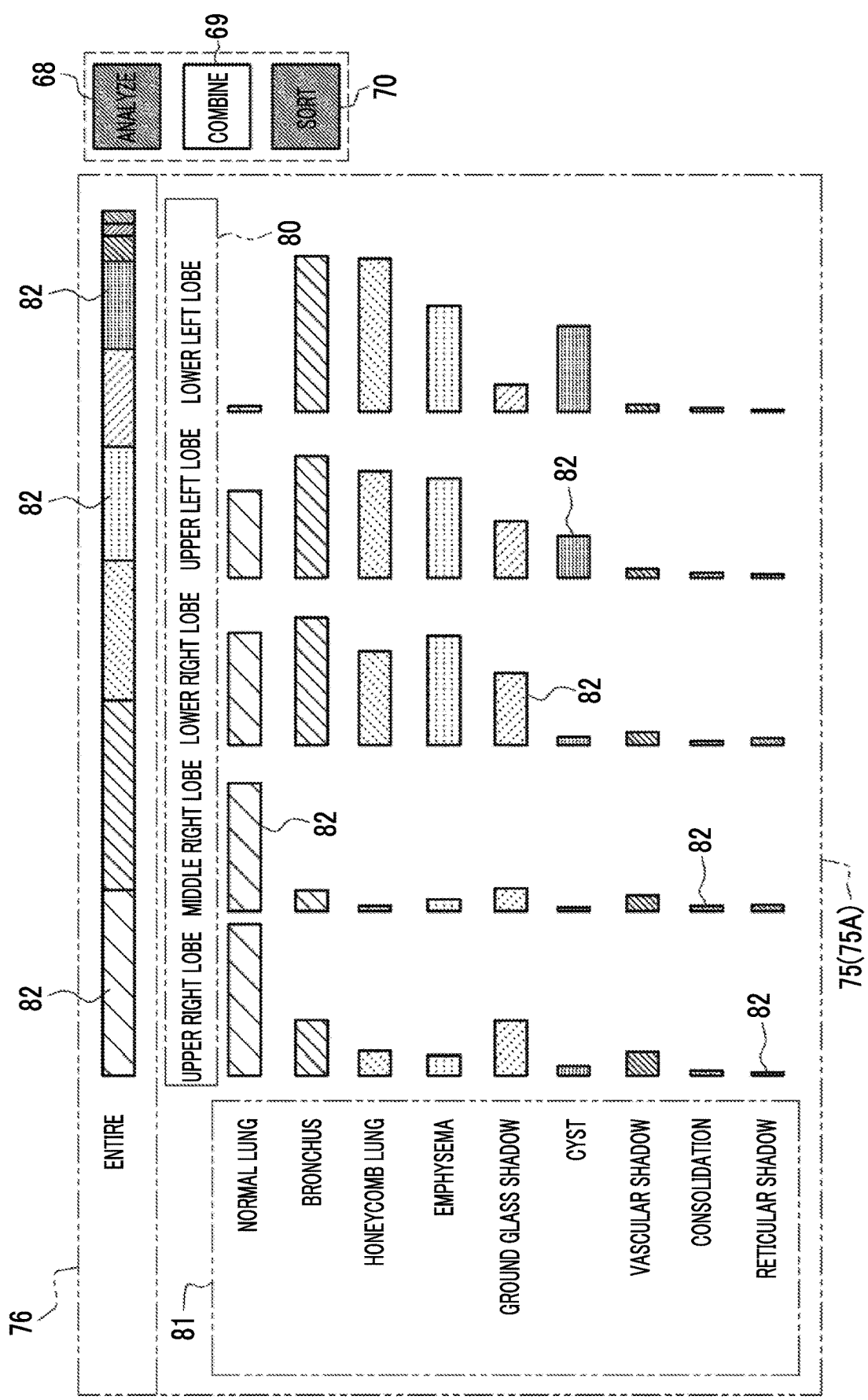
FIG. 12 is a diagram showing a tissue distribution table and an entire tissue proportion display block in a case where a sort instruction icon is selected.

In a case where the sort instruction icon 70 is selected by the cursor 67, the screen output control unit 52 changes the display of the tissue distribution table 75 as shown in FIG. 12. Specifically, the screen output control unit 52 changes the arrangement order of the tissues on the second axis 81 based on the total value of the volume of each tissue. In addition, the screen output control unit 52 also changes the arrangement order of the first bar mark 82 in the entire tissue proportion display block 76 based on the total value of the volume of each tissue.

FIG. 12 shows an example in which the tissues on the second axis 81 and the first bar marks 82 of the entire tissue proportion display block 76 are arranged in descending order of the total value. Specifically, the normal lung with the largest total value is arranged at the top of the second axis 81, and the first bar mark 82 of the normal lung is arranged at the left end of the entire tissue proportion display block 76. Then, the bronchus, the honeycomb lung, the emphysema, . . . are arranged subsequent to the normal lung, and the reticular shadow with the smallest total value is arranged at the bottom of the second axis 81, and the first bar mark 82 of the reticular shadow is arranged at the right end of the entire tissue proportion display block 76. In contrast to the example of FIG. 12, the tissues on the second axis 81 and the first bar marks 82 of the entire tissue proportion display block 76 may be arranged in ascending order of the total value.

In a case where the selection of the sort instruction icon 70 is canceled in FIG. 12, the screen output control unit 52 returns the tissue distribution table 75 to the state of FIG. 10.

Figure 13:
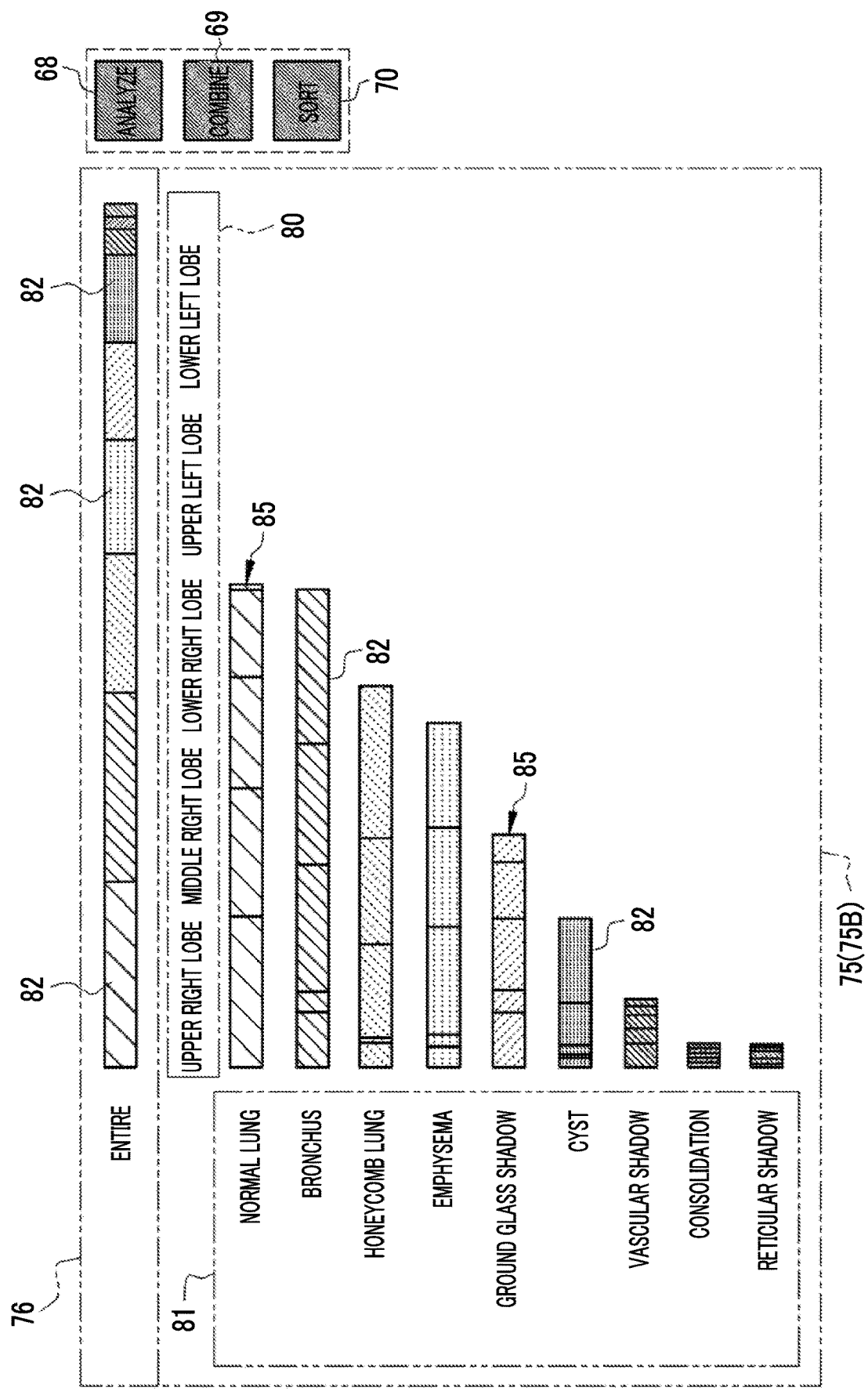
FIG. 13 is a diagram showing a tissue distribution table and an entire tissue proportion display block in a case where a combination instruction icon and a sort instruction icon are selected.

FIG. 13 shows the tissue distribution table 75 in a case where both the combination instruction icon 69 and the sort instruction icon 70 are selected by the cursor 67. In this case, the screen output control unit 52 combines the first bar marks 82 of the respective tissues to form the combined bar mark 85, and changes the arrangement order of the tissues on the second axis 81 and the first bar marks 82 of the entire tissue proportion display block 76.

Hereinafter, the operation of the interpretation support server 16 configured as described above will be described with reference to the flowcharts shown in FIGS. 14 and 15. First, the operation program 45 is activated in the interpretation support server 16. As a result, the reception unit 50, the analysis unit 51, and the screen output control unit 52 are constructed in the CPU 32B of the interpretation support server 16. The computer forming the interpretation support server 16 functions as an interpretation support apparatus.

In the case of interpreting the target image 17A, the doctor DR activates a web browser at the medical department terminal 12 and accesses the interpretation support server 16. A distribution instruction screen for giving an instruction to distribute the viewer screen 60 is displayed on the web browser after accessing the interpretation support server 16. A GUI for designating the target image 17A and a GUI for distribution instruction are provided on the distribution instruction screen. The doctor DR gives an instruction to distribute the viewer screen 60 through the distribution instruction screen. As a result, a request for distribution of the viewer screen 60 is issued from the browser control unit 41 of the medical department terminal 12 to the reception unit 50 of the interpretation support server 16.

Figure 14:
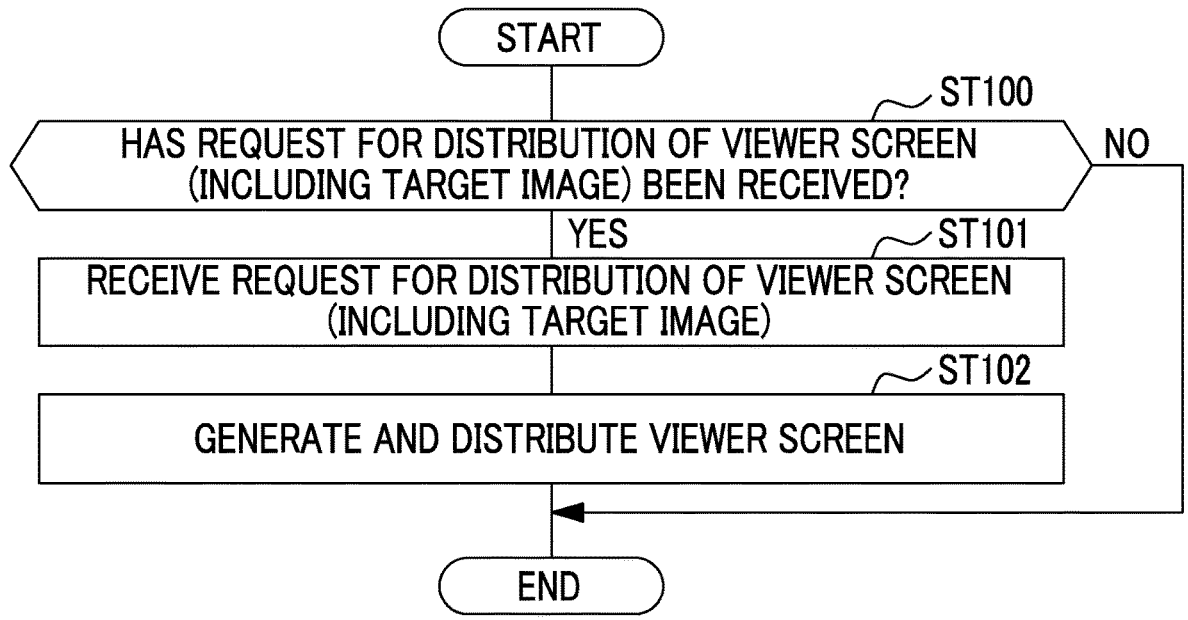
FIG. 14 is a flowchart showing a processing procedure of an interpretation support server.

In FIG. 14, in the interpretation support server 16, the request for distribution of the viewer screen 60 from the medical department terminal 12 is received by the reception unit 50 (YES in step ST100 and step ST101). The request for distribution of the viewer screen 60 includes the target image 17A. Therefore, step ST101 corresponds to a reception step for receiving the target image 17A (medical image 17).

The request for distribution of the viewer screen 60 is output from the reception unit 50 to the screen output control unit 52. The screen output control unit 52 generates the viewer screen 60 shown in FIG. 8, on which the target image 17A included in the distribution request is displayed, based on the viewer screen display data 47. The viewer screen 60 is distributed from the screen output control unit 52 to the medical department terminal 12 that is a source of the request for distribution of the viewer screen 60 (step ST102).

The doctor DR observes the images 17A_A, 17A_S, and 17A_C on the viewer screen 60. In a case where a lesion tissue is found in the target image 17A, the doctor DR selects the analysis instruction icon 68 with the cursor 67 in order to know the distribution of each tissue. As a result, a request for analysis of the target image 17A is issued from the browser control unit 41 of the medical department terminal 12 to the reception unit 50 of the interpretation support server 16.

Figure 15:
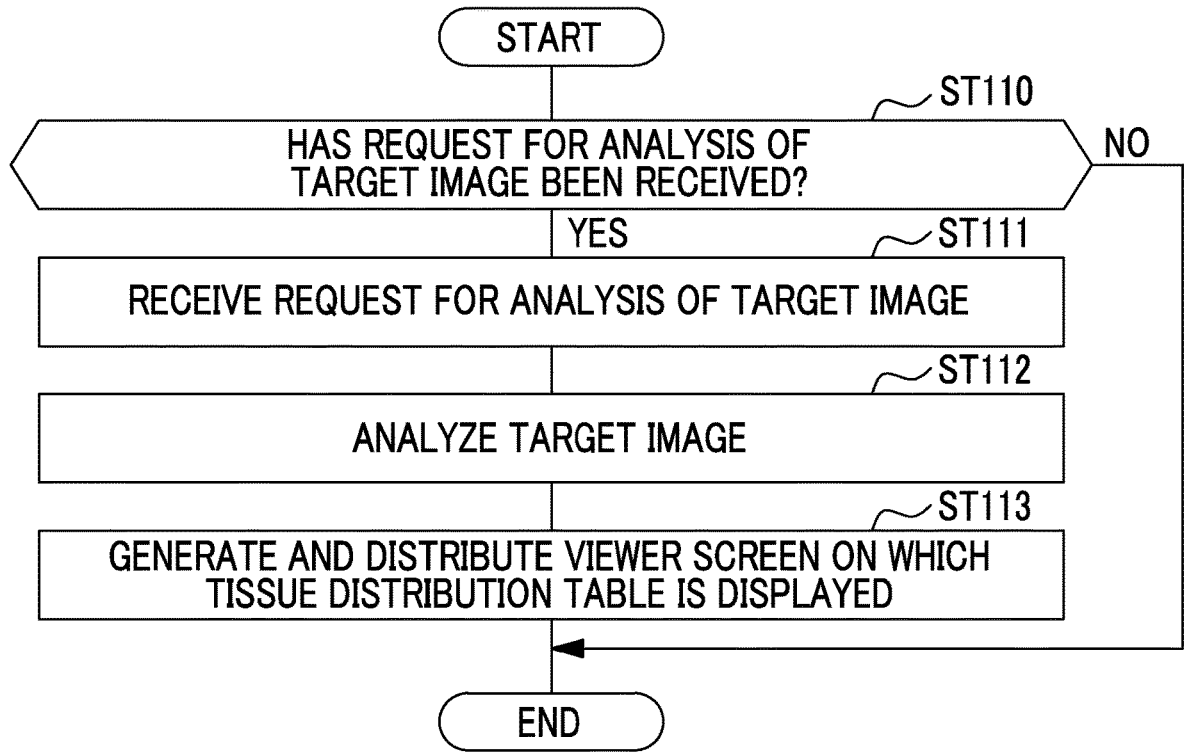
FIG. 15 is a flowchart showing a processing procedure of an interpretation support server.

In FIG. 15, in the interpretation support server 16, the request for analysis of the target image 17A from the medical department terminal 12 is received by the reception unit 50 (YES in step ST110 and step ST111). The request for analysis of the target image 17A is output from the reception unit 50 to the analysis unit 51. The analysis unit 51 determines to which of a plurality of types of tissues each voxel forming the target image 17A belongs based on the tissue determination data 46 shown in FIG. 6 (step ST112, analysis step). The analysis result is output from the analysis unit 51 to the screen output control unit 52.

The screen output control unit 52 generates the viewer screen 60 shown in FIG. 9, on which the tissue distribution table 75 according to the analysis result is displayed, based on the viewer screen display data 47. The viewer screen 60 is distributed from the screen output control unit 52 to the medical department terminal 12 that is a source of the request for analysis of the target image 17A (step ST113, output control step).

The doctor DR views the tissue distribution table 75 at the medical department terminal 12 and knows the distribution of tissues, that is, what kind of and how many tissues are present in which part. Then, the combination instruction icon 69 or the sort instruction icon 70 are selected by the cursor 67 as necessary. In response to these operation instructions, the viewer screen 60 on which the combined tissue distribution table 75B shown in FIGS. 11 and 13 is displayed and the viewer screen 60 on which the tissue distribution table 75, in which the arrangement order of the tissues on the second axis 81 shown in FIGS. 12 and 13 is changed, is displayed is distributed from the screen output control unit 52. The doctor DR records findings on the target image 17A based on the distribution of the tissues grasped through the tissue distribution table 75.

The tissue distribution table 75 has the first axis 80 on which a plurality of parts of the lung are arranged and the second axis 81 on which a plurality of types of tissues are arranged, and the first bar mark 82 expressing the magnitude of the volume of the tissue is arranged in a region surrounded by the first axis 80 and the second axis 81. Therefore, the doctor DR can immediately understand which first bar mark 82 expresses the magnitude of the volume of which tissue in which part just by glancing at the tissue distribution table 75.

In particular, in the discrete tissue distribution table 75A shown in FIGS. 10 and 12 in which the first bar marks 82 are arranged at the intersections between the parts on the first axis 80 and the tissues on the second axis 81, the doctor DR can instantaneously understand which first bar mark 82 expresses the magnitude of the volume of which tissue in which part without any doubt.

Also in the combined tissue distribution table 75B shown in FIGS. 11 and 13 in which the first bar mark 82 is a single combined bar mark 85, the display of the first axis 80 remains unchanged, and the position of the first bar mark 82 moves slightly along the first axis 80. Therefore, the doctor DR can sufficiently understand which first bar mark 82 expresses the magnitude of the volume of which tissue in which part. In addition, in order to make it easier to understand which first bar mark 82 expresses the magnitude of the volume of which tissue in which part, how the first bar marks 82 are combined by leftward filling along the first axis 80 may be shown by animation at the time of switching from the discrete tissue distribution table to the combined tissue distribution table. The parts on the first axis 80 may also be slightly moved in a direction in which the first bar marks 82 are filled.

By viewing the first bar mark 82 along the second axis 81 while fixing the part on the first axis 80, it is possible to see the distribution of the volume of each tissue in the relevant part. For example, in FIG. 10, in the case of the lower left lobe, it can be seen that the volume of normal lung of normal tissue is small and conversely, the volumes of honeycomb lung, emphysema, and cyst of lesion tissue are large. On the contrary, by viewing the first bar mark 82 along the first axis 80 while fixing the tissue part on the second axis 81, it is possible to see the distribution of the volume of each part in the relevant tissue. For example, in FIG. 10, in the case of emphysema, it can be seen that the volumes of the lower right lobe, the upper left lobe, and the lower left lobe are larger than the volumes of the upper right lobe and the middle right lobe.

The screen output control unit 52 switches and outputs the discrete tissue distribution table 75A shown in FIGS. 10 and 12 and the combined tissue distribution table 75B shown in FIGS. 11 and 13 according to the instruction from the doctor DR. Therefore, the doctor DR can grasp the distribution of tissues from a viewpoint according to his or her observation purpose. For example, the doctor DR can check the detailed distribution of each tissue with the discrete tissue distribution table 75A, or can check the total value of the volume of each tissue expressed by the combined bar mark 85 with the combined tissue distribution table 75B.

The combined tissue distribution table 75B may be output first and switched to the discrete tissue distribution table 75A according to an instruction from the doctor DR. At the time of interpretation, the doctor DR first checks which tissue has a certain volume and then views the distribution of each tissue in each part. Therefore, in a case where the combined tissue distribution table 75B is output first and then switched to the discrete tissue distribution table 75A, the interpretation work advances because this matches the order of thinking of the doctor DR.

The total value of the volume of each tissue can be checked in the entire tissue proportion display block 76 once. However, in the combined tissue distribution table 75B, in addition to the total value of the volume of each tissue, the distribution of the volume of each part can also be known by the first bar mark 82 forming each combined bar mark 85. Therefore, the entire tissue proportion display block 76 is suitable for being used for rough grasp of the total value of the volume of each tissue.

As shown in FIGS. 12 and 13, based on the total value of the volume of each tissue, the screen output control unit 52 changes the arrangement order of the tissues on the second axis 81 and changes the arrangement order of the first bar mark 82 in the entire tissue proportion display block 76. Therefore, the doctor DR can grasp at a glance which tissue volume is the largest or smallest. In addition, the doctor DR can grasp the magnitude of the volume of the tissue of interest at a glance. For example, the doctor DR can grasp at a glance whether or not the volume of the honeycomb lung is larger than the volume of the ground glass shadow.

Here, in a case where the sort instruction icon 70 is selected by the cursor 67, the arrangement order of the tissues on the second axis 81 and the arrangement order of the first bar mark 82 in the entire tissue proportion display block 76 are changed based on the total value of the volume of each tissue. However, the invention is not limited thereto. Even in a case where the sort instruction icon 70 is eliminated and there is no sort instruction, the arrangement order of the tissues on the second axis 81 and the arrangement order of the first bar mark 82 in the entire tissue proportion display block 76 may be changed based on the total value of the volume of each tissue, and then the tissue distribution table 75 may be output.

Since the screen output control unit 52 outputs the target image 17A at the same time as the tissue distribution table 75, the interpretation work of the doctor DR advances. In a case where the target image 17A and the tissue distribution table 75 are displayed on different screens, a troublesome operation, such as switching screens, is required, but there is no such concern.

Since the screen output control unit 52 arranges the parts on the first axis 80 along the display direction of the lung in the target image 17A, the doctor DR can easily associate the parts of the lung in the target image 17A with the parts on the first axis 80 in the tissue distribution table 75. In a case where the parts on the first axis 80 do not follow the display direction of the lung in the target image 17A, the doctor DR needs to temporarily organize the correspondence relationship between the parts of the lung in the target image 17A and the parts on the first axis 80 in the tissue distribution table 75 in his or her head, but there is no such concern.

The screen output control unit 52 uses the first axis 80 as the horizontal axis and the second axis 81 as the vertical axis. In particular, in a case where the organ is divided into left and right parts as the lung of this example, the doctor DR can easily associate the parts of the lung in the target image 17A with the parts on the first axis 80 in the tissue distribution table 75 by arranging the parts on the first axis 80 along the display direction of the lung in the target image 17A with the first axis 80 as the horizontal axis. Examples of an organ which is divided into left and right parts include brain, kidney, and the like in addition to the lung of this example.

Organs are not limited to those which are divided into left and right parts. Other organs, such as stomach, liver, and large intestine, may be used. In the case of such organs which are not divided into left and right parts, the first axis 80 may be set as the vertical axis and the second axis 81 may be set as the horizontal axis. Also in this case, however, it is preferable to arrange the parts on the first axis 80 along the display direction of the organ in the target image 17A. For example, in a case where the stomach is shown upside down in the target image 17A, parts of the stomach on the first axis 80 are arranged in order from the bottom.

In a case where the display direction of the organ of the target image 17A is changed on the viewer screen 60, it is preferable that the screen output control unit 52 rearranges the parts on the first axis 80 in conjunction with the change of the display direction of the organ in the target image 17A. For example, in FIG. 9, in a case where the left and right directions of the display directions of the axial image 17A_A and the coronal image 17A_C are reversed, the screen output control unit 52 rearranges the upper left lobe and the lower left lobe, which are on the right side of the first axis 80, on the left side and the upper right lobe, the middle right lobe, and the lower right lobe, which are on the left side of the first axis 80, on the right side.

The screen output control unit 52 outputs the first bar mark 82 in an identifiable form for each tissue by changing the display color of the first bar mark 82 for each tissue. Therefore, just by viewing the first bar mark 82, the doctor DR can roughly understand that the first bar mark 82 expresses the magnitude of the volume of which tissue. In addition, the screen output control unit 52 outputs the tissue on the target image 17A in the same form as the first bar mark 82. Therefore, the doctor DR can easily associate the target image 17A and the tissue distribution table 75.

By changing the display color of the first bar mark 82 for each of a plurality of groups divided according to the pixel value of the voxel, the screen output control unit 52 outputs the first bar mark 82 in an identifiable form for each of the plurality of groups. Therefore, in the case of performing interpretation focusing on the distribution of tissues of each group, the doctor DR can grasp the distribution of tissues of each group at a glance.

The screen output control unit 52 outputs the first bar mark 82 arranged in the normal tissue and the first bar mark 82 arranged in the lesion tissue in identifiable forms by changing the display colors of the first bar marks 82. Therefore, the doctor DR can grasp the approximate distribution of the normal tissue and the lesion tissue at a glance, such as the proportion of the lesion tissue to the normal tissue.

As a method of outputting each first bar mark 82 in an identifiable form, instead of or in addition to changing the display color, various methods may be adopted such as changing the pattern, changing the thickness of the frame of the bar, or dividing each tissue, each group, and normal tissue and lesion tissue with a boundary line parallel to the first axis 80.

Second Embodiment

Figure 16:
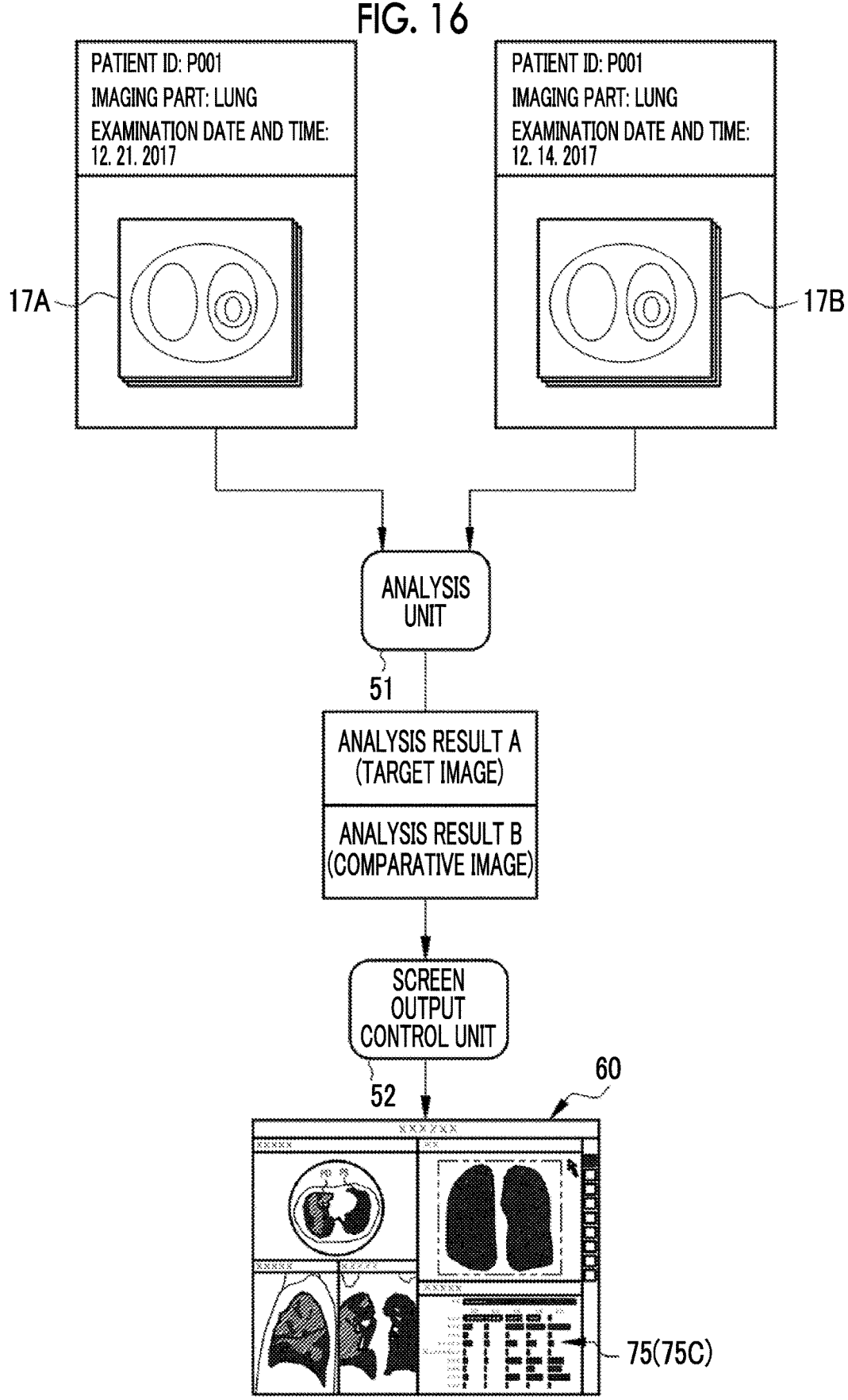
FIG. 16 is a diagram showing a state in which an analysis unit analyzes a comparative image and a screen output control unit generates and outputs a viewer screen, on which a comparative tissue distribution table is displayed, based on the analysis result.
Figure 17:
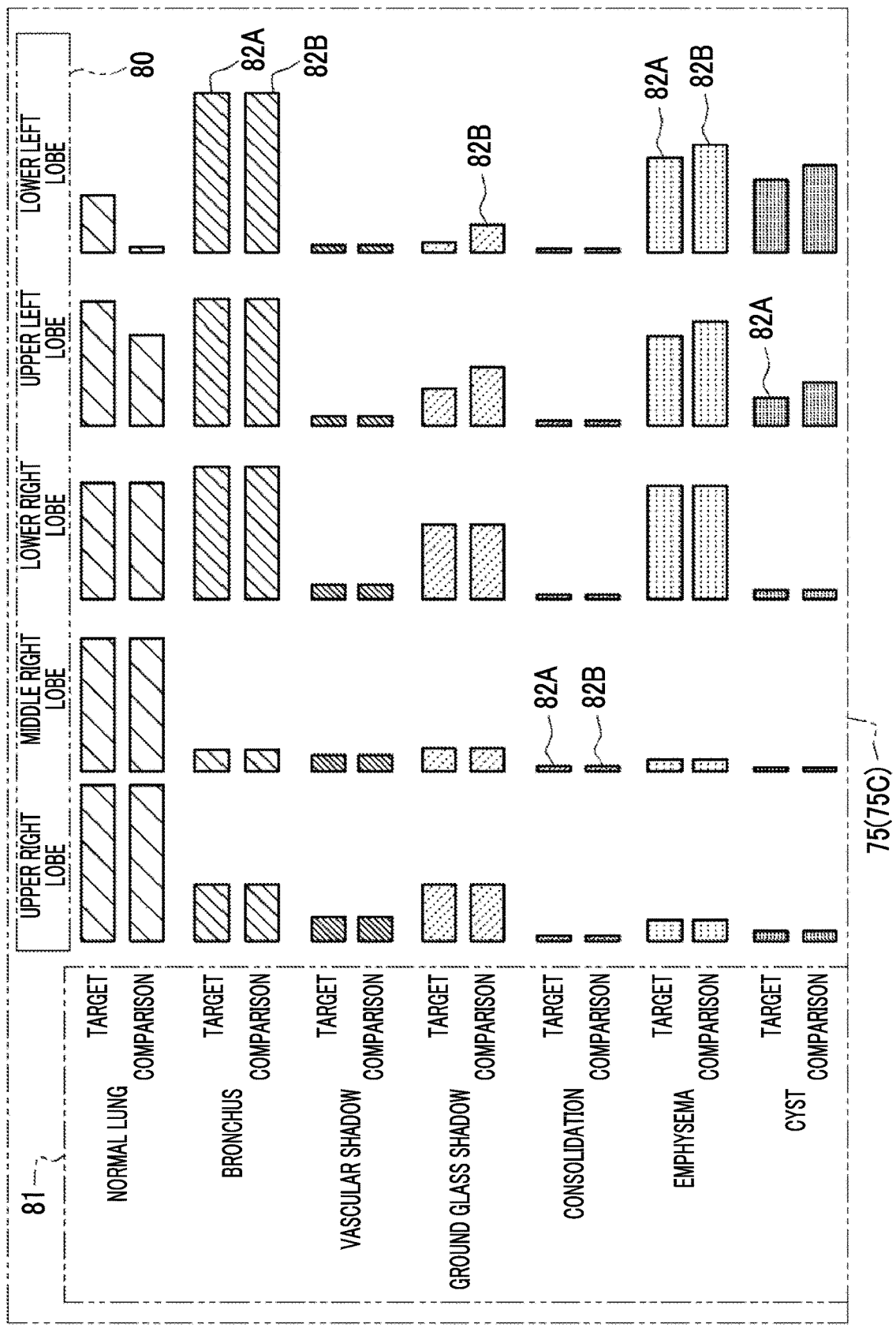
FIG. 17 is a diagram showing a comparative tissue distribution table.

In a second embodiment shown in FIGS. 16 and 17, the screen output control unit 52 outputs a comparative tissue distribution table 75C that is the tissue distribution table 75 in which a plurality of first bar marks 82 having different medical images 17 to be analyzed are arranged.

In FIG. 16, in the second embodiment, the analysis unit 51 analyzes not only the target image 17A but also a comparative image 17B to determine to which of the tissues each voxel of the comparative image 17B belongs. In addition to an analysis result A of the target image 17A, the analysis unit 51 outputs an analysis result B of the comparative image 17B to the screen output control unit 52. The screen output control unit 52 generates the viewer screen 60, on which the comparative tissue distribution table 75C is displayed, based on the analysis results A and B, and distributes the viewer screen 60 to the medical department terminal 12.

The comparative image 17B is obtained by imaging the organ (here, the lung) of the same patient (patient ID: P001) as the target image 17A at different dates and times (the target image 17A is 2017. 12. 21, and the comparative image 17B is 2017. 12. 14) from the target image 17A. The comparative image 17B is designated by, for example, inputting an image ID to a dialog appearing by selecting a dedicated icon on the tool bar 66 with the cursor 67.

In FIG. 17, in the comparative tissue distribution table 75C, a first bar mark 82A based on the analysis result A of the target image 17A and a first bar mark 82B based on the analysis result B of the comparative image 17B are arranged up and down in each tissue. The first bar marks 82A and 82B correspond to a plurality of marks having different medical images 17 to be analyzed. The display positions of the first bar marks 82A and 82B are divided up and down, but the display colors in each tissue are the same.

In FIG. 17, the honeycomb lung and the reticular shadow are not shown due to the shortage of space. In addition, the entire tissue proportion display block 76 is not shown either. In the entire tissue proportion display block 76 in this case, two first bar marks for the target image 17A and the comparative image 17B are displayed similar to first bar marks 82A and 82B.

In this manner, since the screen output control unit 52 outputs the comparative tissue distribution table 75C in which a plurality of first bar marks 82A and 82B having different medical images 17 to be analyzed are arranged, it is possible to easily compare the distribution of tissues in the target image 17A with the distribution of tissues in the comparative image 17B.

The comparative image 17B and the target image 17A to be analyzed of the first bar marks 82A and 82B are obtained by imaging the lung of the same patient at different dates and times. For this reason, the first bar marks 82A and 82B expresses the temporal transition of the volume of each tissue. Therefore, for example, in a case where the examination purpose is a follow-up observation, the doctor DR can instantaneously determine how the volume of each tissue has changed before and after applying medical treatments, such as surgery or medication.

In the first embodiment described above, the number of voxels belonging to each tissue in each part is expressed by the length of the first bar mark 82 along the first axis 80. On the other hand, in the second embodiment, it is preferable that the proportion of the number of voxels belonging to each tissue in each part or the proportion of the number of voxels belonging to each part in each tissue is expressed by the lengths of the first bar marks 82A and 82B along the first axis 80.

The proportion of the number of voxels belonging to each tissue in each part is a value obtained by dividing the number of voxels belonging to each tissue by the number of all voxels belonging to each part. For example, in a case where the number of all voxels belonging to the part of the upper right lobe of the lung is 1000 and the number of voxels belonging to the normal lung is 800, the proportion of the number of voxels belonging to the normal lung in the part of the upper right lobe is 800/1000=0.8.

Similarly, the proportion of the number of voxels belonging to each part in each tissue is a value obtained by dividing the number of voxels belonging to each part by the number of all voxels belonging to each tissue. For example, in a case where the number of all voxels belonging to the honeycomb lung is 500 and the number of voxels belonging to the lower left lobe is 150, the proportion of the number of voxels belonging to the lower left part in the honeycomb lung is 150/500=0.3.

As described above, in a case where the proportion of the number of voxels belonging to each tissue in each part or the proportion of the number of voxels belonging to each part in each tissue is expressed by the lengths of the first bar marks 82A and 82B along the first axis 80, there are the following effects. That is, since the difference between the lengths of the first bar marks 82A and 82B along the first axis 80 directly indicates how much the volume of each tissue in the target image 17A and the comparative image 17B has increased or decreased, this is particularly suitable for follow-up observation focusing on the temporal transition of the proportion of the volume of each tissue.

Although not shown, the comparative tissue distribution table 75C is also switched from the state of the discrete tissue distribution table shown in FIG. 17 to the combined tissue distribution table by selection of the combination instruction icon 69 as in the first embodiment described above. In addition, by the selection of the sort instruction icon 70, the arrangement order of the tissues on the second axis 81 and the arrangement order of the first bar marks 82A and 82B in the entire tissue proportion display block 76 are changed.

There is one comparative image 17B, and a plurality of marks are two first bar marks 82A and 82B. However, two or more comparative images 17B may be used, and accordingly, a plurality of marks may be three or more marks.

The medical images 17 to be analyzed of a plurality of marks are not limited to those obtained by imaging the organ of the same patient at different dates and times as described above. For example, a similar patient whose attributes, such as sex or age, are the same as those of the target patient and whose medical image 17 is similar to the target image 17A is searched for. Then, the mark based on the analysis result of the medical image 17 of the similar patient may be displayed side by side with the mark based on the analysis result of the target image 17A.

The mark expressing the magnitude of the volume of the tissue is not limited to the first bar mark 82 in each of the embodiments described above. For example, the mark expressing the magnitude of the volume of the tissue may be a mark shown in each of FIGS. 18 and 19.

Figure 18:
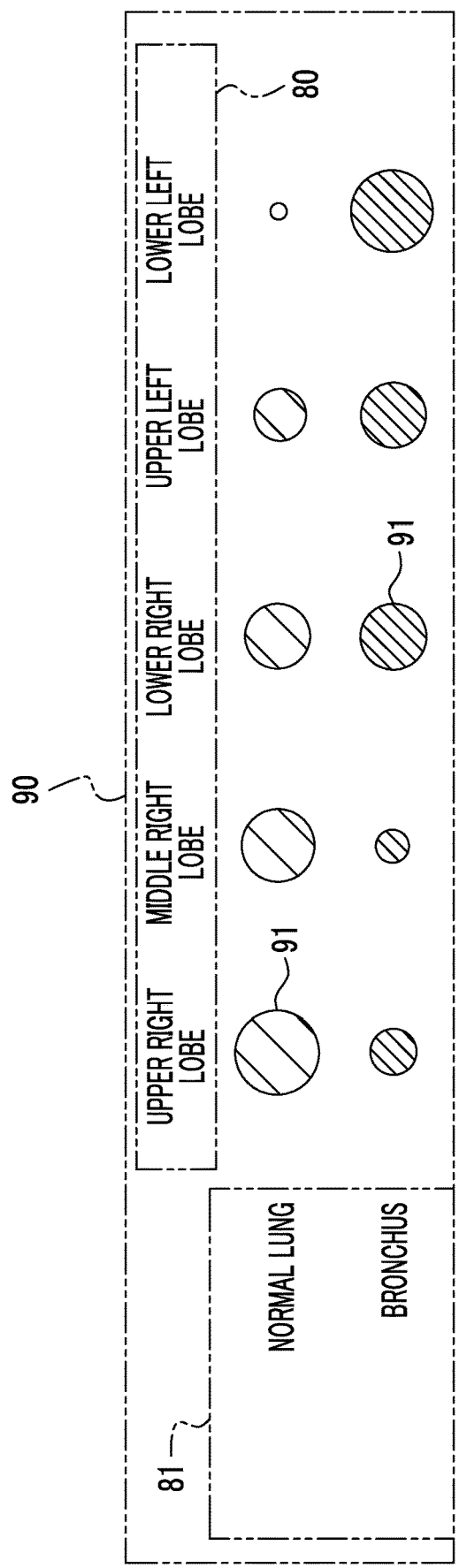
FIG. 18 is a diagram showing a tissue distribution table using a circle mark.

In a tissue distribution table 90 shown in FIG. 18, a circle mark 91 is used as a mark expressing the magnitude of the volume of the tissue. The circle mark 91 expresses the volume of the tissue with its size. That is, the volume of the tissue is large in a case where the circle mark 91 is large, and the volume of the tissue is small in a case where the circle mark 91 is small.

Figure 19:
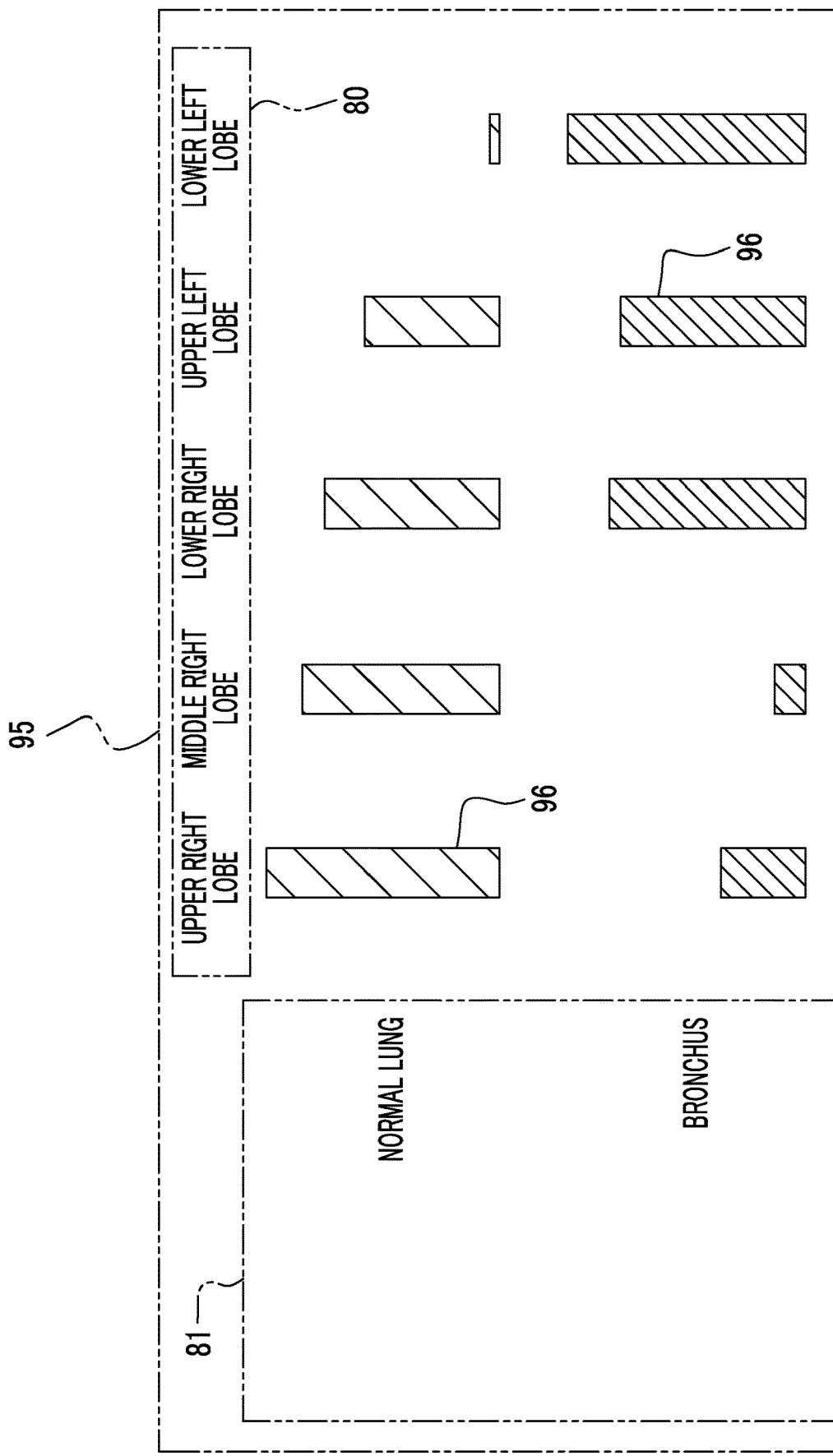
FIG. 19 is a diagram showing a tissue distribution table using a second bar mark.

In a tissue distribution table 95 shown in FIG. 19, a second bar mark 96 is used as a mark expressing the magnitude of the volume of the tissue. The second bar mark 96 expresses the volume of the tissue with a length along the second axis 81. That is, the volume of the tissue is large in a case where the length along the second axis 81 is large, and the volume of the tissue is small in a case where the length along the second axis 81 is small. In FIGS. 18 and 19, tissues other than the normal lung and the bronchus are not shown.

The sizes of the circle mark 91 and the second bar mark 96 in the direction along the first axis 80 are smaller than the size of the first bar mark 82 in the direction along the first axis 80. Accordingly, the sizes of the tissue distribution tables 90 and 95 in the direction along the first axis 80 can be reduced as compared with the tissue distribution table 75. In the case of the circle mark 91 and the second bar mark 96, there is only the discrete tissue distribution table and the combined tissue distribution table is not output.

The doctor DR may select which of the first bar mark 82, the circle mark 91, and the second bar mark 96 is to be used as a mark.

Figure 20:
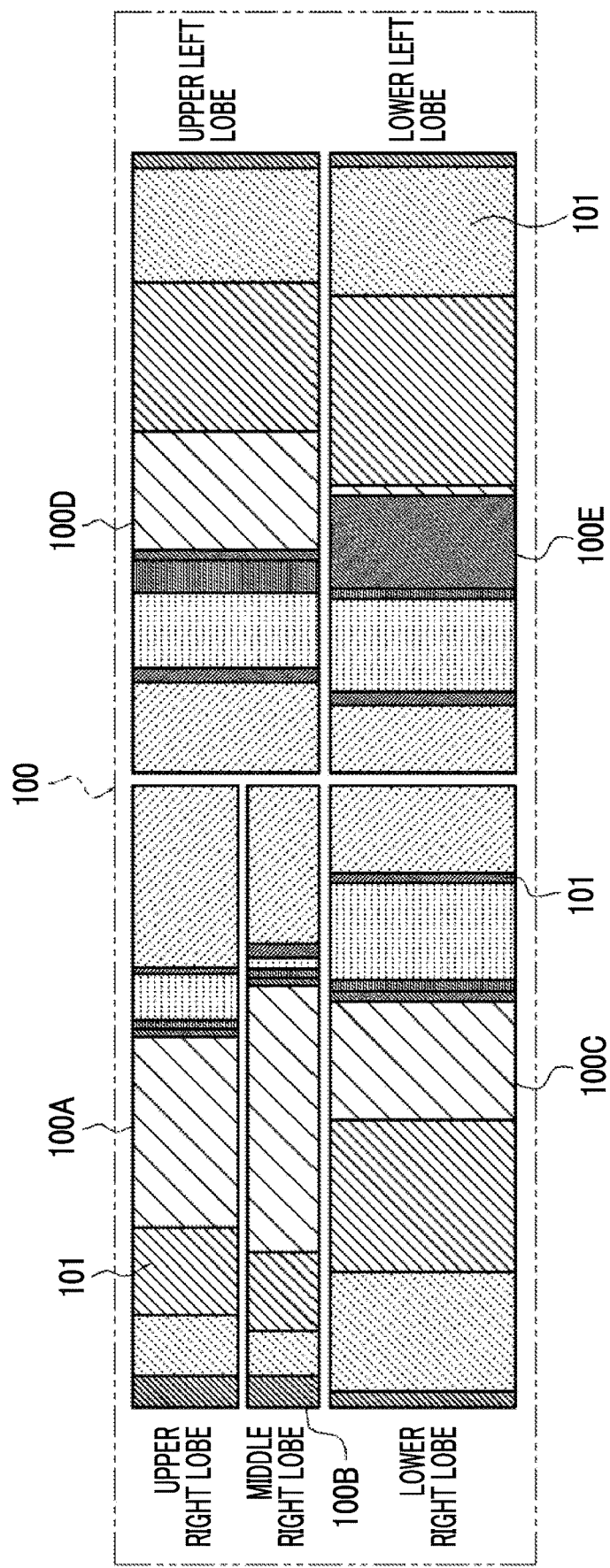
FIG. 20 is a diagram showing a part-specific tissue proportion display block.

The screen output control unit 52 may output a part-specific tissue proportion display block 100 shown in FIG. 20. The part-specific tissue proportion display block 100 is configured to include an upper right lobe block 100A, a middle right lobe block 100B, a lower right lobe block 100C, an upper left lobe block 100D, and a lower left lobe block 100E. Each of the blocks 100A to 100E has segments 101 divided into the number of tissues. The segment 101 expresses the proportion of the volume of each tissue occupying each part with a length along the horizontal direction.

The length of each of the blocks 100A to 100E in the vertical direction is proportional to the volume of each part. Accordingly, the lengths of the blocks 100C and 100E of the lower right lobe and the lower left lobe, which have approximately the same volume, in the vertical direction are approximately the same. In addition, the middle right lobe block 100B having the smallest volume has the shortest length in the vertical direction. In the segment 101, vascular shadow, honeycomb lung, bronchus, normal lung, cyst, reticular shadow, emphysema, consolidation, and ground glass shadow are arranged in this order from the end to the center of each part.

In the part-specific tissue proportion display block 100, the length of each of the blocks 100A to 100E in the vertical direction changes in proportion to the volume of each part. For this reason, there is a disadvantage that it is difficult to distinguish between the sizes of the segments 101. However, the part-specific tissue proportion display block 100 is suitable for the doctor DR to grasp the outline of the distribution of tissues.

The tissue distribution table 75 and the part-specific tissue proportion display block 100 may be switched and output according to an instruction from the doctor DR.

Parts and tissues are not limited to those exemplified in the respective embodiments described above. For example, in a case where the organ is a stomach, parts are a cardia, a gastric fundus, a gastric body, a vestibular part, a pylorus, and the like. Instead of or in addition to the nine types of tissues mentioned in each of the above embodiments, an infiltrative shadow, a tumor shadow, a nodule shadow, a linear shadow, a dot shadow, a pneumothorax, a bra, a cavity, bronchial wall thickening, traction bronchiectasis, bronchial permeability, pleural thickening, pleural effusion, and the like may be adopted.

The arrangement order of the tissues on the second axis 81 before changing the arrangement order according to the selection of the sort instruction icon 70 can be appropriately changed. For example, in the first embodiment described above, normal tissues and lesion tissues are displayed in this order. However, lesion tissues and normal tissues may be displayed in this order conversely. At the time of interpretation, the doctor DR focuses on lesion tissues. Therefore, by displaying the lesion tissues and the normal tissues in this order, the normal tissue to which the doctor DR does not pay much attention is moved away to the lower part of the second axis 81. Similarly for the arrangement order of the first bar mark 82 in the entire tissue proportion display block 76, lesion tissues may be located on the left side, and normal tissues may be moved away to the right side.

In the first embodiment described above, all the tissues are targets whose arrangement order is to be changed according to the selection of the sort instruction icon 70. However, normal tissues may be excluded from the targets, and the arrangement order of only the lesion tissues may be changed. This is because, for the same reason as above, it is considered that there is no influence on the majority even in a case where normal tissues to which the doctor DR does not pay much attention are excluded from the targets whose arrangement order is to be changed.

In the first embodiment described above, the analysis unit 51 starts the analysis of the target image 17A after a request for analysis of the target image 17A by the selection of the analysis instruction icon 68 is received by the reception unit 50. However, the present invention is not limited thereto. The analysis unit 51 may start the analysis of the target image 17A at a point in time at which a request for distribution of the viewer screen 60 is received by the reception unit 50. In this case, the analysis instruction icon 68 is not necessary.

In each of the embodiments described above, the interpretation support apparatus according to the embodiment of the invention has been described in the form of the interpretation support server 16 that performs processing based on various requests from the medical department terminal 12. However, the medical department terminal 12 may be made to have a function of the interpretation support apparatus. In this case, each processing unit, such as the analysis unit 51, is constructed in the CPU of the medical department terminal 12.

The medical image DB server 15 and the interpretation support server 16 may be configured as separate servers as shown in FIG. 1, or may be integrated into one server.

In order to improve the processing capacity or reliability, the interpretation support server 16 may be formed by a plurality of server computers that are separated from each other as hardware. For example, as a server computer having the functions of the reception unit 50 and the analysis unit 51 and a server computer having the function of the screen output control unit 52, respective processing units are distributed to a plurality of server computers. In this case, the plurality of server computers correspond to the interpretation support apparatus.

Thus, the hardware configuration of a computer system can be appropriately changed according to the required performance, such as processing capacity, safety, or reliability. Needless to say, in order to ensure the safety or reliability, an application program, such as the operation program 45, may be duplicated or may be stored in a plurality of storage devices in a distributed manner, without being limited to hardware.

In each of the embodiments described above, the medical information system 2 constructed in the medical facility is exemplified, and the interpretation support server 16 is used in one medical facility. However, the interpretation support server 16 may be configured to be usable in a plurality of medical facilities.

In each of the embodiments described above, the interpretation support server 16 is communicably connected to a client terminal, such as the medical department terminal 12 installed in one medical facility, through the network 18, such as a LAN, and provides an application service called distribution of the viewer screen 60 in response to a request from the client terminal. In order to make the interpretation support server 16 available in a plurality of medical facilities, the interpretation support server 16 is communicably connected to each client terminal installed in the plurality of medical facilities, for example, through the Internet or a wide area network (WAN), such as a public communication network. Then, the interpretation support server 16 receives a request from each client terminal in the plurality of medical facilities through the Internet or a WAN, such as a public communication network, and provides an application service for distributing the viewer screen 60 to each client terminal. In the case of using a WAN, it is preferable to construct a virtual private network (VPN) or to use a communication protocol with a high security level, such as hypertext transfer protocol secure (HTTPS), in consideration of information security.

In this case, the installation location and management entity of the interpretation support server 16 may be a data center managed by a company that is different from the medical facilities, or may be one of the plurality of medical facilities, for example.

The invention is not limited to each of the embodiments described above, and it is needless to say that various configurations can be adopted without departing from the scope of the invention.

The output form of the tissue distribution table is not limited to the viewer screen 60 exemplified in each of the above embodiments, and includes printing out onto a paper medium or file output using e-mail or the like. Therefore, the output control unit may be a printout control unit or a file output control unit.

In each of the embodiments described above, the hardware structure of a processing unit that performs various kinds of processing, such as the reception unit 50, the analysis unit 51, and the screen output control unit 52, is, for example, the CPU 32B that is a general-purpose processor that executes software (operation program 45) to function as various processing units.

Instead of all or some of the functions realized by the CPU 32B, the following various processors may be used. For example, the various processors include a programmable logic device (PLD) that is a processor whose circuit configuration can be changed after manufacture, such as a field programmable gate array (FPGA), and a dedicated electric circuit that is a processor having a dedicated circuit configuration for executing specific processing, such as an application specific integrated circuit (ASIC). More specifically, the hardware structure of these various processors is an electrical circuit (circuitry) in the form of a combination of circuit elements, such as semiconductor elements.

From the above description, it is possible to grasp the invention shown in the following supplementary item.

Supplementary Item 1

An interpretation support apparatus comprising: a reception processor that receives a medical image having three-dimensional information of an organ; an analysis processor that analyzes the medical image to determine to which of a plurality of types of tissues each voxel forming the medical image belongs; and an output control processor that controls an output of a tissue distribution table having a first axis on which a plurality of parts of the organ are arranged, a second axis which is perpendicular to the first axis and on which the tissues are arranged, and a mark that is arranged in a region surrounded by the first and second axes and expresses a magnitude of a volume of each of the tissues according to an analysis result of the analysis processor.

It is also possible to appropriately combine the above-described various embodiments or various modification examples. In addition to the program, the invention also extends to a storage medium for storing the program.

EXPLANATION OF REFERENCES

2: medical information system
10: medical department
11: examination department
12: medical department terminal
13: modality
14: order management terminal
15: medical image database (DB) server
16: interpretation support server (interpretation support apparatus)
17: medical image
17A: target image
17A_A: axial image
17A_S: sagittal image
17A_C: coronal image
17A_3D: three-dimensional image
17B: comparative image
18: network
19: medical image database (DB)
30: storage device
31: memory
32, 32A, 32B: CPU
33, 33A: display
34, 34A: input device
35: communication unit
36: data bus
40: GUI control unit
41: browser control unit
45: operation program
46: tissue determination data
47: viewer screen display data
47A: layout data
47B: GUI data
47C: display color data
50: reception unit
51: analysis unit
52: screen output control unit
60: viewer screen
61: axial image display region
62: sagittal image display region
63: coronal image display region
64: first analysis result display region
65: second analysis result display region
66: tool bar
67: cursor
68: analysis instruction icon
69: combination instruction icon
70: sort instruction icon
75, 90, 95: tissue distribution table
75A: discrete tissue distribution table
75B: combined tissue distribution table
75C: comparative tissue distribution table
76: entire tissue proportion display block
80: first axis
81: second axis
82, 82A, 82B: first bar mark 85: combined bar mark
91: circle mark
96: second bar mark
100: part-specific tissue proportion display block
100A: upper right lobe block
100B: middle right lobe block
100C: lower right lobe block
100D: upper left lobe block
100E: lower left lobe block
101: segment
DR: doctor
PD: right lung
PS: left lung
ST1 to ST9, ST100 to ST102, ST110 to ST113: step

What is claimed is:

1. An interpretation support apparatus, comprising:
a reception unit that receives a medical image having three-dimensional information of an organ;
an analysis unit that analyzes the medical image to determine to which of a plurality of types of tissues each voxel forming the medical image belongs; and
an output control unit that controls an output of a tissue distribution table having a first axis on which a plurality of parts of the organ are arranged, a second axis which is perpendicular to the first axis and on which the tissues are arranged, and a mark that is arranged in a region surrounded by the first and second axes and expresses a magnitude of a volume of each of the tissues according to an analysis result of the analysis unit.

2. The interpretation support apparatus according to claim 1,
wherein the output control unit outputs a discrete tissue distribution table in which the mark is arranged at an intersection between each of the parts and each of the tissues.

3. The interpretation support apparatus according to claim 1,
wherein the mark is one of a circle mark expressing the volume with its size, a first bar mark expressing the volume with a length along the first axis, or a second bar mark expressing the volume with a length along the second axis.

4. The interpretation support apparatus according to claim 3,
wherein the mark is the first bar mark, and
the output control unit switches and outputs a discrete tissue distribution table in which the mark is arranged at an intersection between each of the parts and each of the tissues and a combined tissue distribution table in which a combined bar mark, which is obtained by combining the first bar marks along the first axis and expresses a total value of the volume of each of the tissues, is arranged according to an instruction from an operator.

5. The interpretation support apparatus according to claim 3,
wherein the output control unit outputs an entire tissue proportion display block, which expresses a proportion of the tissue in the entire organ with the first bar mark, at the same time as the tissue distribution table.

6. The interpretation support apparatus according to claim 1,
wherein the output control unit changes an arrangement order of the tissues on the second axis based on a total value of the volume of each of the tissues.

7. The interpretation support apparatus according to claim 6,
wherein the output control unit outputs an entire tissue proportion display block, which expresses a proportion of the tissue in the entire organ with the first bar mark, at the same time as the tissue distribution table, and changes an arrangement order of the first bar mark in the entire tissue proportion display block based on the total value.

8. The interpretation support apparatus according to claim 1,
wherein the output control unit outputs a comparative tissue distribution table in which a plurality of marks having different medical images to be analyzed are arranged.

9. The interpretation support apparatus according to claim 8,
wherein the medical images to be analyzed of the plurality of marks are obtained by imaging the organ of the same patient at different dates and times.

10. The interpretation support apparatus according to claim 1,
wherein the output control unit outputs the medical image at the same time as the tissue distribution table.

11. The interpretation support apparatus according to claim 10,
wherein the output control unit arranges the parts on the first axis along a display direction of the organ in the medical image.

12. The interpretation support apparatus according to claim 10,
wherein the output control unit uses the first axis as a horizontal axis and the second axis as a vertical axis.

13. The interpretation support apparatus according to claim 12,
wherein the organ is a lung.

14. The interpretation support apparatus according to claim 1,
wherein the output control unit outputs the mark in an identifiable form for each of the tissues.

15. The interpretation support apparatus according to claim 14,
wherein the output control unit outputs the medical image at the same time as the tissue distribution table, and outputs the tissues on the medical image in the same form as the mark.

16. The interpretation support apparatus according to claim 14,
wherein the tissues are divided into a plurality of groups according to a pixel value of the voxel, and
the output control unit outputs the mark in an identifiable form for each of the groups.

17. The interpretation support apparatus according to claim 14,
wherein the tissues include a normal tissue and a lesion tissue, and
the output control unit outputs the marks arranged in the normal tissue and the marks arranged in the lesion tissue in identifiable forms.

18. An operation method of an interpretation support apparatus, comprising:
a reception step of receiving a medical image having three-dimensional information of an organ;
an analysis step of analyzing the medical image to determine to which of a plurality of types of tissues each voxel forming the medical image belongs; and an output control step of controlling an output of a tissue distribution table having a first axis on which a plurality of parts of the organ are arranged, a second axis which is perpendicular to the first axis and on which the tissues are arranged, and a mark that is arranged in a region surrounded by the first and second axes and expresses a magnitude of a volume of each of the tissues according to an analysis result in the analysis step.

19. A non-transitory computer readable medium for storing a computer-executable program for execution of interpretation support, the computer-executable program causing a computer to execute:

a reception function for receiving a medical image having three-dimensional information of an organ;

an analysis function for analyzing the medical image to determine to which of a plurality of types of tissues each voxel forming the medical image belongs; and an output control function for controlling an output of a tissue distribution table having a first axis on which a plurality of parts of the organ are arranged, a second axis which is perpendicular to the first axis and on which the tissues are arranged, and a mark that is arranged in a region surrounded by the first and second axes and expresses a magnitude of a volume of each of the tissues according to an analysis result of the analysis function.

* * * * *